US007001735B2

(12) United States Patent
Charron et al.

(10) Patent No.: US 7,001,735 B2
(45) Date of Patent: Feb. 21, 2006

(54) GLUCOSE TRANSPORTER/SENSOR PROTEIN AND USES THEREOF

(75) Inventors: Maureen J. Charron, Flushing, NY (US); Ellen B. Katz, Port Washington, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 13 days.

(21) Appl. No.: 09/886,954

(22) Filed: Jun. 21, 2001

(65) Prior Publication Data

US 2002/0038464 A1 Mar. 28, 2002

Related U.S. Application Data

(63) Continuation-in-part of application No. 09/516,493, filed on Mar. 1, 2000, now abandoned.

(51) Int. Cl.
  *G01N 33/574* (2006.01)
  *G01N 33/53* (2006.01)
  *G01N 33/48* (2006.01)
  *C12Q 1/68* (2006.01)

(52) U.S. Cl. .......................... 435/7.23; 435/7.1; 435/6; 436/64

(58) Field of Classification Search ........... 435/4–7.23; 424/9.1; 436/64
See application file for complete search history.

(56) References Cited

U.S. PATENT DOCUMENTS

| | | | |
|---|---|---|---|
| 5,942,398 A | | 8/1999 | Tartaglia et al. |
| 6,136,547 A | | 10/2000 | Tartaglia et al. |
| 2003/0171275 A1 * | | 9/2003 | Baughn et al. ............... 514/12 |

FOREIGN PATENT DOCUMENTS

| | | | |
|---|---|---|---|
| WO | WO 99/18125 | * | 4/1999 |
| WO | WO 01/04145 A2 | | 1/2001 |
| WO | WO 200190304 A2 | * | 11/2001 |

OTHER PUBLICATIONS

Dermer (Bio/Technology, 1994, 12:320).*
Tockman et al (Cancer Res., 1992, 52:2711s-2718s).*
Slamon et al. (Science vol. 235, Jan. 1987, pp. 177-182).*
U.S. Appl. No. 60/172000.*
U.S. Appl. No. 60/176083.*
U.S. Appl. No. 60/177332.*
U.S. Appl. No. 60/172572.*
U.S. Appl. No. 60/173758.*
U.S. Appl. No. 60/181625.*
Goldman et al. "Regulated Expression of the Novel Glucose Transport Facilitator, GLUTx1, in Proliferative Endometrium and Endometrial Adenocarcinoma" Abstract #5033, Proceedings of the American Association for Cancer Research, vol. 42, Mar. 2001.*

Ausubel et al., Short Protocols in Molecular Biology, Third Edition, pp. 16-3—16-5, 16-58—16-62, 1995.
Bruning, et al., A muscle-specific insulin receptor knockout exhibits features of the metabolic syndrome of NIDDM without altering glucose tolerance. Mol Cell, 2:559-69, 1998.
Calderhead et al., Insulin regulation of the two glucose transporters in 3T3-L1 adipocytes. J Biol Chem, 265: 13800-08, 1990.
Cartee, et al., Stimulation of glucose transport in skeletal muscle by hypoxia. J Appl Physiol, 70:1593-1600, 1991.
Chan and Exton, A rapid method of the determination of glycogen content and radioactivity in small quantities of tissue or isolated hepatocytes. Anal Biochem, 71:96-105, 1976.
Chang, et al., Overexpression of hexokinase II in transgenic mice. J Biol Chem, 271:14834-39, 1996.
Cushman and Salans, Determinations of adipose cell size and number in suspensions of isolated rat and human adipose cells. J Lipid Res, 19:269-73, 1978.
Devaskar and Mueckler, The mammalian glucose transporters. Pediatr Res, 31:1-13, 1992.
Doege et al., Glut8, a novel member of the sugar transport facilitator family with glucose transport activity. J Biol Chem, 275:16275-80, 2000.
Douen et al., Exercise Induces Recruitment of the Insulin-responsive glucose transporter. J Biol Chem, 265:13427-30, 1990.
Foley, Rationale and application of fatty acid oxidation inhibitors in treatment of diabetes mellitus. Diabetes Care, 15:773-84, 1992.
Froehner et al., The blood-nerve barrier is rich in glucose transporter. J Neurocytol, 17:173-178, 1988.
Garcia De Herreros and Birnbaum, The acquisition of increased insulin-responsive hexose transport in 3T3- L1 adipocytes correlates with expression of a novel transporter gene. J Biol Chem, 264:19994-99, 1989.

(Continued)

*Primary Examiner*—Gary B. Nickol
(74) *Attorney, Agent, or Firm*—Amster, Rothstein & Ebenstein LLP

(57) ABSTRACT

The present invention provides a method for determining whether a subject has a defect in cell proliferation. The present invention further provides a method for assessing the efficacy of therapy to treat a defect in cell proliferation in a subject who has undergone or is undergoing treatment for a defect in cell proliferation. Also provided by the present invention is a method for assessing the prognosis of a subject who has a defect in cell proliferation. Additionally, the present invention provides a method for treating a defect in cell proliferation in a subject in need of treatment thereof by inhibiting GLUTx. The present invention also provides methods for treating ischemia in a subject in need of treatment thereof. Finally, the present invention provides a method for treating infertility in a subject in need of treatment thereof.

11 Claims, 13 Drawing Sheets

OTHER PUBLICATIONS

Gumáet al. Insulin induces translocation of GLUT-4 glucose transportes in human skeletal muscle. Am J Physiol, 268: E613-E622, 1995.

Hansen, et al., Suitability of 2-deoxyglucose for in vitro measurement of glucose transport activity in skeletal muscle. J Appl Physiol, 76:979-85, 1994.

Hellwig, et al., Localization of the binding domain of the inhibitory ligand forskolin in the glucose transporter GLUT -4 by photolabeling, proteolytic cleavage and a site-specific antiserum. Biochim Biophys Acta, 1111:178-84, 1992.

Heydrick, et al., Early alteration of insulin stimulation of PI 3-kinase in muscle and adipocyte from gold thioglucose obese mice. Am J physiol, 268:E604-12, 1995.

Hirshman et al., Identification of an intracellular pool of glucose transporters from basal and insulin-stimulated rat skeletal muscle. J Biol Chem, 265:987-91, 1990.

Holloszy and Booth, Biochemical Adaptions to endurance exerecise in muscle. Annu Rev Physiol, 38:273-91, 1976.

Holman, et al., Cell surface labeling of glucose transporter isoform GLUT4 by bis-mannose photolabel. J Bio Chem, 265:18172-79, 1990.

Hurley et al., Muscle triglyceride utilization during exercise: effect of training. J Appl Physiol, 60:562-67, 1986.

Ibberson et al., GLUTX1, a novel mammalian gluocose transporter expressed in central nervous system and insulin-sensitive tissues. The Journal of Biological Chemistry, 275: 4607-12, 2000.

Jenkins et al., Effects of nonesterified fatty acid availability on tissue-specific glucose utilization in rats in vivo. J Chin Invest., 82:293-99, 1988.

Joost et al., Structure-function relationship of glucose transporters catalyzing facilitated diffusion. Exp Clin Endocrinol, 102:434-38, 1994.

Kahn, Glucose transport: pivotal step in insulin action. Diabetes, 45:1644-54, 1996.

Kamohara et al. Acute stimulation of glucose metabolism in mice by leptin treatment.

Katz, et al., Cardiac and adipose tissue abnormalities but not diabetes in mice deficient in GLUT4. Nature, 377:151-55, 1995.

Klip et al., Insulin-induced translocation of glucose transporters in rat hindlimb muscles. FEBS letters, 224:224-30, 1987.

Lee et al., Comparative expressed-sequence-tag analysis or differential gene expression profiles in PC-12 cells before and after nerve growth factor treatment. Proc. Natl. Acad. Sci USA, 92:8303-07, 1995.

Massillon et al., Quantitation of hepatic glucose fluxes and pathways of hepatic glycogen synthesis in conscious mice. Am J Physiol, 269:E1037-1043, 1995.

Murakami et al., Enzymatic and genetic adaption of soleus muscle mitochondria to physical training in rats. Am J Physiol, 267:E388-E395, 1994.

Nakatani et al., Effect of endurance exercise training on muscle glycogen supercompensation in rats. J Appl Physiol, 82:711-15, 1997.

Oakes et al., A new antidiabetic agent, BRL 49653, reduces lipid availability and improves insulin action and glucoregulation in the rat. Diabetes, 43:1203-10, 1994.

Okuno et al., Acute effect of troglitazone on glucose metabolism in the absence of presence of insulin in perfused rat hindlimb. Metabolism, 46:716-21, 1997.

Olson and Pessin, Structure, function, and regulation of the mammalian faclitative glucose transporter gene family. Annu Rev Nutr, 16:235-56, 1996.

Ozcan et al., Two glucose transporters in Saccharomyces cerevisiae are glucose sensors that generate a signal for induction of gene expression. Proc Natl Acad Sci U S A, 93:12428-32, 1996.

Ozcan et al., Glucose sensing and signaling by two glucose receptors in the yeast Saccharomyces cerevisiae, EMBO J, 17:2566-73, 1998.

Postic et al., The effects of hyperinsulinemia and hyperglycemia on GLUT4 and hexokinase II mRNA and protein in rat skeletal muscle and adipose tissue. Diabetes, 42:922-929, 1993.

Randle et al., The glucose fatty-acid cycle in role in insulin sensitivity and the metabolic disturbances of diabetes mellitus. Lancet, 1:785-89, 1963.

Romijn et al., Regulation of endogenus fat and carboydrate metabolism in relation to exercise intensity and duration. Am J Physiol, 265:E380-91, 1993.

Schurmann et al., Glucose transport activity and photolabeling with 3-[125I]iodo-4-azidophenethylamido-7-0-succinyldeacetyl (IAPS)-forskolin of two mutants at tryptophan-38B and -412 of the glucose transporter GLUT 1: dissociation of the binding domains of forskolin and glucose. Biochem J, 290:497-501, 1993.

Shepherd et al., Adipose cell hyperplasia and enhanced glucose disposal in transgenic mice overexpressing GLUT4 selectively in adipose tissue. J Biol Chem, 268:22243-46, 1993.

Stenbit et al., Diverse effects of GLUT4 ablation on glucose uptake and glycogen synthesis in red and white skeletal muscle. J Clin Invest, 98:629-34, 1996.

Stenbit et al., GLUT4 heterozygous knockout mice develop muscle insulin resistance and diabetes. Nature Med, 3:1096-1101, 1997.

Tsao et al., Enhanced insulin action due to targeted GLUT4 overexpression exclusively in muscle. Diabetes, 45:28-36, 1996.

Tsao et al., Muscle-specific transgenic complementation of GLUT4-deficient mice. J Clin Invest, 100: 671-677, 1997.

Wibom et al., Adaption of mitochondrial ATP production in human skeletal muscle to endurance training and detraining. J Appl Physiol, 73:2004-10, 1992.

Wilson et al., Regulation of cell surface GLUT1, GLUT3, and GLUT4 by insulin and IGF-I in L6 myotubes. FEBS Lett, 368: 19-22, 1995.

Zierath et al., Restoration of hypoxia-stimulated glucose uptake in GLUT4-deficient muscles by muscle-specific GLUT4 transgenic complementation. J Biol Chem, 273: 20910-15, 1998.

Zorzano et al., Insulin-regulated glucose uptake in rat adipocytes is mediated by two transporter isoforms present in at least two vesicle populations. J Biol Chem 264: 12358-63, 1989.

Reagan et al., Localization and regulation of GLUTx1 glucose transporter in the hippocampus of streptoztochin diabetic rats. PNAS, 98: 2820-2825, 2001.

Ngo, Computational complexity Protein structure prediction and the Levinthal paradox in The Protein Folding Problem and Tertiary Structure Prediction, Merz et al. (eds.) Birkhauser Boston: MA, pp. 433 and 492-495, 1994.

Rudinger Characteristics of amino as components of a peptide hormone sequence (in Peptide Hormones, Parsons (ed.), University Park Press: Baltimore, MD, pp. 1-7, 1976.

* cited by examiner

SEQUENCE LISTING

```
<160> NUMBER OF SEQ ID NOS: 1

<210> SEQ ID NO 1
<211> LENGTH: 477
<212> TYPE: PRT
<213> ORGANISM: Homo sapiens
```

<400> SEQUENCE: 1

```
Met Thr Pro Glu Asp Pro Glu Thr Gln Pro Leu Leu Gly Pro Pro
1               5                   10                  15

Gly Gly Ser Ala Pro Arg Gly Arg Val Phe Leu Ala Ala Phe Ala
            20                  25                  30

Ala Ala Leu Gly Pro Leu Ser Phe Gly Phe Ala Leu Gly Tyr Ser Ser
        35                  40                  45

Pro Ala Ile Pro Ser Leu Gln Arg Ala Ala Pro Pro Ala Pro Arg Leu
        50                  55                  60

Asp Asp Ala Ala Ala Ser Trp Phe Gly Ala Val Val Thr Leu Gly Ala
65                  70                  75                  80

Ala Ala Gly Gly Val Leu Gly Gly Trp Leu Val Asp Arg Ala Gly Arg
                85                  90                  95

Lys Leu Ser Leu Leu Leu Cys Ser Val Pro Phe Val Ala Gly Phe Ala
                100                 105                 110

Val Ile Thr Ala Ala Gln Asp Val Trp Met Leu Leu Gly Gly Arg Leu
            115                 120                 125

Leu Thr Gly Leu Ala Cys Gly Val Ala Ser Leu Val Ala Pro Val Tyr
    130                 135                 140

Ile Ser Glu Ile Ala Tyr Pro Ala Val Arg Gly Leu Leu Gly Ser Cys
145                 150                 155                 160

Val Gln Leu Met Val Val Gly Ile Leu Leu Ala Tyr Leu Ala Gly
                165                 170                 175

Trp Val Leu Glu Trp Arg Trp Leu Ala Val Leu Gly Cys Val Pro Pro
                180                 185                 190

Ser Leu Met Leu Leu Met Cys Phe Met Pro Glu Thr Pro Arg Phe
        195                 200                 205

Leu Leu Thr Gln His Arg Arg Gln Glu Ala Met Ala Ala Leu Arg Phe
    210                 215                 220

Leu Trp Gly Ser Glu Gln Gly Trp Glu Asp Pro Pro Ile Gly Ala Glu
225                 230                 235                 240

Gln Ser Phe His Leu Ala Leu Leu Arg Gln Pro Gly Ile Tyr Lys Pro
                245                 250                 255

Phe Ile Ile Gly Val Ser Leu Met Ala Phe Gln Gln Leu Ser Gly Val
                260                 265                 270

Asn Ala Val Met Phe Tyr Ala Glu Thr Ile Phe Glu Glu Ala Lys Phe
                275                 280                 285

Lys Asp Ser Ser Leu Ala Ser Val Val Gly Val Ile Gln Val Leu
    290                 295                 300

Phe Thr Ala Val Ala Ala Leu Ile Met Asp Arg Ala Gly Arg Arg Leu
305                 310                 315                 320

Leu Leu Val Leu Ser Gly Val Val Met Val Phe Ser Thr Ser Ala Phe
                325                 330                 335

Gly Ala Tyr Phe Lys Leu Thr Gln Gly Gly Pro Gly Asn Ser Ser His
                340                 345                 350

Val Ala Ile Ser Ala Pro Val Ser Ala Gln Pro Val Asp Ala Ser Val
            355                 360                 365

Gly Leu Ala Trp Leu Ala Val Gly Ser Met Cys Leu Phe Ile Ala Gly
    370                 375                 380

Phe Ala Val Gly Trp Gly Pro Ile Pro Trp Leu Leu Met Ser Glu Ile
385                 390                 395                 400
```

-continued

```
Phe Pro Leu His Val Lys Gly Val Ala Thr Gly Ile Cys Val Leu Thr
            405                 410                 415

Asn Trp Leu Met Ala Phe Leu Val Thr Lys Glu Phe Ser Ser Leu Met
            420                 425                 430

Glu Val Leu Arg Pro Tyr Gly Ala Phe Trp Leu Ala Ser Ala Phe Cys
        435                 440                 445

Ile Phe Ser Val Leu Phe Thr Leu Phe Cys Val Pro Glu Thr Lys Gly
    450                 455                 460

Lys Thr Leu Glu Gln Ile Thr Ala His Phe Glu Gly Arg
465                 470                 475
```

GLUCOSE TRANSPORTER/SENSOR PROTEIN AND USES THEREOF

CROSS-REFERENCE TO RELATED APPLICATION

This application is a continuation-in-part of U.S. patent application Ser. No. 09/516,493, filed Mar. 1, 2000, now abandoned the entire contents of which are expressly incorporated by reference herein.

BACKGROUND OF THE INVENTION

GLUT4 is the predominant facilitative glucose transporter expressed in such insulin-responsive tissues as adipose tissue and cardiac and skeletal muscle (2, 19). Under basal conditions, GLUT4 is sequestered from the plasma membrane in a unique intracellular compartment. In response to various stimuli (e.g., insulin, contraction, hypoxia), GLUT4 translocates to the cell surface and is mostly responsible for the increase in glucose uptake (20–24).

In a previous study, the insulin-sensitive glucose transporter, GLUT4, was genetically ablated in mice (1). Unexpectedly, GLUT4-null mice were able to maintain normal glycemia with moderate fed hyperinsulinemia, even though in vitro studies showed the null muscle to be highly insulin resistant (1, 3). Interestingly, oxidative soleus muscle of female GLUT4-null mice retained a significant insulin-stimulated glucose uptake (3). Furthermore, skeletal muscle of GLUT4-null mice maintained normal levels of high energy phosphate pools (25). However, unlike serum glucose level, fed serum free fatty acids and fasted ketone body levels were significantly decreased in GLUT4-null mice (1). The compensatory glucose uptake response was more robust in vivo under hyperglycemic clamp conditions, thereby suggesting that a glucose-sensitive glucose transport system or glucose sensor/receptor-like molecule was activated in highly oxidative tissues in the absence of GLUT4.

Cloning efforts have led to the isolation of a novel cDNA encoding GLUTx (4–7), a protein which is also referred to as GLUTx1 and GLUT8. GLUTx has significant homology to facilitative glucose transporters such as GLUT4 and GLUT1, and has conserved amino acids known to be important in glucose binding. Additionally, GLUTx contains amino acid motifs present only in the glucose sensor/receptors SNF3 and RGT2. Using in situ hybridization techniques, GLUTx has been detected in the cerebellum and hippocampus of GLUT4-null and wild-type mice, and in other areas corresponding to the "obesity center" of the human brain (e.g., the hypothalamus). These findings suggest that GLUTx functions as a glucose sensor/receptor that assists in maintenance of normal blood glucose.

SUMMARY OF THE INVENTION

The present invention is based upon the discovery that GLUTx is overexpressed in tumors and in other stressed environments where oxygen and/or nutrients may be lacking or in high demand. This discovery has broad implications in the diagnosis, treatment, and monitoring of many conditions associated with high-stress environments, including cancer, ischemia, and male and female infertility.

Accordingly, it is an object of the present invention to provide a method for determining whether a subject has a defect in cell proliferation, by assaying a diagnostic sample of the subject for GLUTx expression, wherein detection of GLUTx expression elevated above normal is diagnostic of a defect in cell proliferation.

It is also an object of the present invention to provide a method for assessing the efficacy of therapy to treat a defect in cell proliferation in a subject who has undergone or is undergoing treatment for a defect in cell proliferation, by assaying a diagnostic sample of the subject for GLUTx expression, wherein detection of GLUTx expression elevated above normal in the diagnostic sample is indicative of a need to continue therapy to treat the defect in cell proliferation, and normal GLUTx expression in the diagnostic sample is indicative of successful therapy.

It is a further object of the present invention to provide a method for assessing the prognosis of a subject who has a defect in cell proliferation, by assaying a diagnostic sample of the subject for GLUTx expression, wherein the subject's prognosis improves with a decrease in GLUTx expression in the diagnostic sample, the subject's prognosis worsens with an increase in GLUTx expression in the diagnostic sample, the subject's prognosis is favorable at normal levels of GLUTx expression in the diagnostic sample, and the subject's prognosis is unfavorable at high levels of GLUTx expression in the diagnostic sample.

Additionally, it is an object of the present invention to provide a method for treating a defect in cell proliferation in a subject in need of treatment thereof by inhibiting GLUTx.

It is a further object of the present invention to provide a method for treating ischemia in a subject in need of treatment thereof, by administering to the subject an amount of GLUTx effective to treat the ischemia in the subject.

It is also an object of the present invention to provide a method for treating ischemia in a subject in need of treatment thereof, comprising administering to the subject an amount of a GLUTx modulator effective to treat the ischemia in the subject.

Finally, it is an object of the present invention to provide a method for treating infertility in a subject in need of treatment thereof, by administering to the subject an amount of GLUTx or a modulator of GLUTX expression effective to treat the infertility in the subject.

Additional objects of the present invention will be apparent from the description which follows.

DETAILED DESCRIPTION OF THE INVENTION

Figure 1:
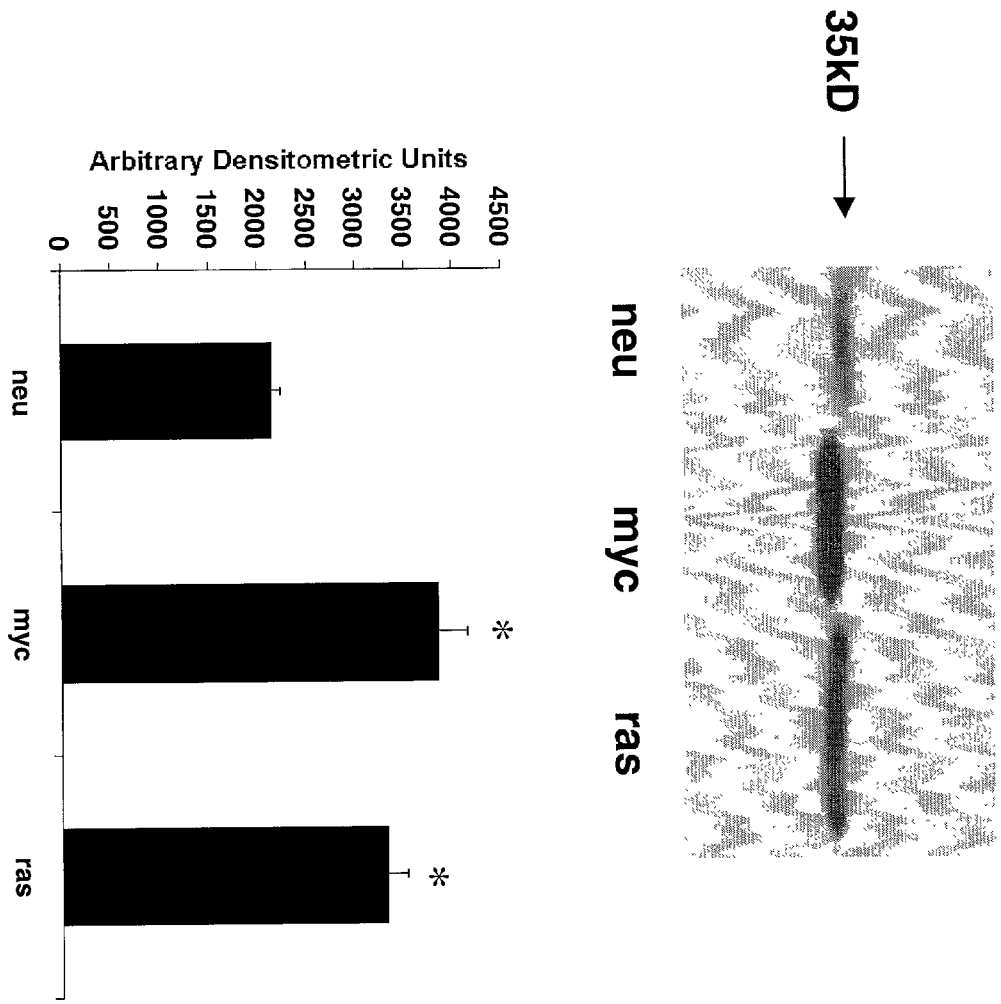
FIG. 1 presents an immunoblot (upper panel) and an immunoblot analysis (lower panel) of GLUTx in mouse mammary tumors. The GLUTx was induced by the overexpression of oncogenes neu, myc, and ras, that were driven by the mouse mammary tumor (MMTV) promoter. The myc and ras oncogenes are involved in regulating glucose metabolism in tumors. The myc and ras tumors had significantly more GLUTx than did the tumors overexpressing neu. GLUTx is shown at approximately 35 kD. *=p<0.05

The present invention provides a method for determining whether a subject has a defect in cell proliferation. As used herein, the "subject" is a mammal, including, without limitation, a cow, dog, human, monkey, mouse, pig, or rat. Preferably, the subject is a human. The method of the present invention comprises assaying a diagnostic sample of the subject for expression of GLUTx, wherein detection of GLUTx expression elevated above normal is diagnostic of a defect in cell proliferation.

Unless otherwise indicated, "GLUTx" includes a GLUTx protein and a "GLUTx analogue", and also refers to GLUTx1 and GLUT8. As used herein, the "GLUTx protein" has the amino acid sequence corresponding to Genbank accession number XP_011828. A "GLUTx analogue", as used herein, is a functional variant of the GLUTx protein, having GLUTx biological activity, that has 60% or greater (preferably, 70% or greater) amino-acid-sequence homology with the GLUTx protein. A "GLUTx analogue" includes a variant of the GLUTx protein that has a homologous three-dimensional conformation. As further used herein, the term "GLUTx biological activity" refers to the activity of a protein or peptide that demonstrates an ability to function as an insulin-responsive and glycemia-sensitive glucose transporter, glucose sensor, or glucose receptor. GLUTx and GLUTx analogues may be produced synthetically or recombinantly, or may be isolated from native cells. GLUTx is preferably produced recombinantly, using conventional techniques and cDNA encoding GLUTx (Genbank accession number XM_011828).

Overexpression of GLUTx may be associated with defects in cell proliferation, while deficient expression of GLUTx may contribute to problems coincident with ischemia, male and female infertility, and other conditions of high stress where nutrients and/or oxygen often are lacking. As used herein, "defect in cell proliferation" refers to an abnormality in cell proliferation, including an abnormality in the arrangement, development, morphology, multiplication, number, organization, proliferation, shape, or size of cells. Examples of defects in cell proliferation include, without limitation, hyperplasia, pre-neoplastic lesions, and neoplasia. As used herein, "hyperplasia" refers to the abnormal multiplication or increase in the number of normal cells, in normal arrangement, within a particular tissue. As further used herein, a "pre-neoplastic lesion" refers to a lesion in cells that has the biologic potential to become neoplastic. Examples of pre-neoplastic lesions in cells include, without limitation, atypia and dysplasia. "Atypia" refers to irregular or nonconforming cells. "Dysplasia" refers to the abnormal development of cells, particularly the pathologic alteration in size, shape, and organization of adult cells (e.g., premalignant mammary gland atypia/dysplasia).

As used herein, "neoplasia" refers to the uncontrolled and progressive multiplication of cells under conditions that would not elicit, or would cause cessation of, multiplication of normal cells. Neoplasia results in the formation of a "neoplasm", which is defined herein to mean any new and abnormal growth, particularly a new growth of tissue, in which the growth of cells is uncontrolled and progressive. Neoplasms include benign tumors and malignant tumors (e.g., carcinomas, including adenocarcinomas such as mammary adenocarcinoma and endometrial adenocarcinoma; lymphocytic leukemias; myeloid leukemias; lymphomas; and melanomas) that are either invasive or noninvasive. Malignant neoplasms are distinguished from benign in that the former show a greater degree of anaplasia, or loss of differentiation and orientation of cells, and have the properties of invasion and metastasis. Thus, neoplasia includes "cancer", which herein refers to a proliferation of tumor cells in tissue having the unique trait of loss of normal controls, resulting in unregulated growth, lack of differentiation, local tissue invasion, and/or metastasis. In one embodiment of the present invention, the neoplasia is mammary adenocarcinoma. In another embodiment of the present invention, the neoplasia is endometrial adenocarcinoma.

In the method of the present invention, a diagnostic sample of a subject may be assayed for GLUTx expression either in vitro or in vivo. In accordance with the present invention, where the assay is performed in vitro, a diagnostic sample from the subject may be removed using standard procedures. The diagnostic sample may be any tissue, particularly blood, bone, brain tissue, endometrial tissue, kidney tissue, mammary tissue, muscle tissue, nervous tissue, or soft tissue, and may be removed by standard biopsy. In one embodiment of the present invention, the tissue is mammary gland tissue. In another embodiment of the present invention, the tissue is endometrial tissue. In addition, the diagnostic sample may be a bodily fluid, including cerebrospinal fluid, pericardial fluid, peritoneal fluid, saliva, serum, and urine. Additionally, the diagnostic sample taken from the subject or patient may be, for example, any tissue known to have a defect in cell proliferation, any tissue suspected of having a defect in cell proliferation, or any tissue believed not to have a defect in cell proliferation.

Protein to be assayed may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (with an antibody to GLUTx), and precipitation (e.g., with isopropanol and a reagent such as Trizol). Isolation and purification of the protein may be followed by electrophoresis (e.g., on an SDS-polyacrylamide gel). Nucleic acid may be isolated from a diagnostic sample using standard techniques known to one of skill in the art.

In accordance with the method of the present invention, a defect in cell proliferation in a subject may be diagnosed by assaying a diagnostic sample of the subject for expression of GLUTx. Because GLUTx is generally expressed only at low levels in cells of healthy, nondiseased subjects (i.e., those who do not have a defect in cell proliferation), apart from cells of the male reproductive organs (as disclosed below), detection of GLUTx expression elevated above normal in a diagnostic sample of a subject is diagnostic of a defect in cell proliferation. As used herein, "expression" means the transcription of the GLUTx gene into at least one mRNA transcript, or the translation of at least one mRNA into a GLUTx protein, as defined above. Accordingly, a diagnostic sample may be assayed for GLUTx expression by assaying for GLUTx protein (as defined above), GLUTx cDNA, or GLUTx mRNA. The appropriate form of GLUTx will be apparent based on the particular techniques discussed herein.

As used herein, "GLUTx expression elevated above normal" means expression of GLUTx at a level that is significantly greater than the level expected for the same type of diagnostic sample taken from a nondiseased subject or patient (i.e., one who does not have a defect in cell proliferation) of the same gender and of similar age. As further used herein, "significantly greater" means that the difference between the level of GLUTx expression that is elevated above normal, and the expected (normal) level of GLUTx, is of statistical significance. Preferably, GLUTx expression elevated above normal is expression of GLUTx at a level that is at least 10% greater than the level of GLUTx expression otherwise expected. Where GLUTx expression is expected to be absent from a particular diagnostic sample taken from a particular subject or patient, the normal level of GLUTx expression for that subject or patient is nil. Where a particular diagnostic sample taken from a particular subject or patient is expected to have a low level of constitutive GLUTx expression, that low level is the normal level of GLUTx expression for that subject or patient.

Expected or normal levels of GLUTx expression for a particular diagnostic sample taken from a subject or patient may be easily determined by assaying nondiseased subjects of a similar age and of the same gender. For example, diagnostic samples may be obtained from at least 30 normal, healthy men and at least 30 normal, healthy women between the ages of 25 and 80, to determine the normal quantity of GLUTx expression in males and females.

Once the above-described samples have been obtained, the normal quantities of GLUTx expression in men and women may be determined using a standard assay for quantification, such as flow cytometry, Western blot analysis, or an ELISA for measuring protein quantities, as described below. For example, an ELISA may be run on each sample in duplicate, and the means and standard deviations of the quantity of the GLUTx protein may be determined. If necessary, additional subjects may be recruited before the normal quantities of GLUTx expression are quantified.

In accordance with the method of the present invention, a diagnostic sample of a subject may be assayed for GLUTX expression, and GLUTX expression may be detected in a diagnostic sample, using assays and detection methods readily determined from the known art, including, without limitation, immunological techniques, hybridization analysis, fluorescence imaging techniques, and/or radiation detection. For example, according to the method of the present invention, a diagnostic sample of the subject may be assayed for GLUTx expression using an agent reactive with GLUTx protein or GLUTx nucleic acid.

As used herein, "reactive" means the agent has affinity for, binds to, or is directed against GLUTx protein or GLUTx nucleic acid. As further used herein, an "agent" shall include a protein, polypeptide, peptide, nucleic acid (including DNA or RNA), antibody, Fab fragment, F(ab')$_2$ fragment, molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion. Preferably, the agent of the present invention is labeled with a detectable marker. Agents that are reactive with GLUTx protein or nucleic acid may be identified by contacting GLUTx protein or nucleic acid with an agent of interest and assessing the ability of the agent to bind to the GLUTx protein or GLUTx nucleic acid.

In one embodiment of the present invention, the agent reactive with GLUTx is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with purified GLUTx. Monoclonal antibody then may be produced by removing the spleen from the immunized mouse, and fusing the spleen cells with myeloma cells to form a hybridoma which, when grown in culture, will produce a monoclonal antibody.

The antibodies used herein may be labeled with a detectable marker. Labeling of an antibody may be accomplished using one of a variety of labeling techniques, including peroxidase, chemiluminescent labels known in the art, and radioactive labels known in the art. The detectable marker of the present invention may be, for example, a nonradioactive or fluorescent marker, such as biotin, fluorescein (FITC), acridine, cholesterol, or carboxy-X-rhodamine (ROX), which can be detected using fluorescence and other imaging techniques readily known in the art. Alternatively, the detectable marker may be a radioactive marker, including, for example, a radioisotope. The radioisotope may be any isotope that emits detectable radiation, such as $^{35}S$, $^{32}P$, or $^{3}H$. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody labeled with a detectable marker.

Where the agent of the present invention is an antibody reactive with GLUTx, a diagnostic sample taken from the subject may be purified by passage through an affinity column which contains GLUTx antibody as a ligand attached to a solid support such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The GLUTx antibody may be further attached to the solid support through a spacer molecule, if desired. Appropriate binding conditions (e.g., temperature, pH, and salt concentration) may be readily determined by the skilled artisan. In a preferred embodiment, the GLUTx antibody is attached to a sepharose column, such as Sepharose 4B.

Where the agent is an antibody, a diagnostic sample of the subject may be assayed for GLUTx expression using binding studies that utilize one or more antibodies immunoreactive with GLUTx, along with standard immunological detection techniques. For example, the GLUTx protein eluted from the affinity column may be subjected to an ELISA assay, Western blot analysis, flow cytometry, or any other immunostaining method employing an antigen-antibody interaction. Preferably, the diagnostic sample is assayed for GLUTx expression using Western blotting.

Alternatively, a diagnostic sample of a subject may be assayed for GLUTx expression using hybridization analysis of nucleic acid extracted from the diagnostic sample taken from the subject. According to this method of the present invention, the hybridization analysis may be conducted using Northern blot analysis of mRNA. This method also may be conducted by performing a Southern blot analysis of DNA using at least one nucleic acid probe which hybridizes to nucleic acid encoding GLUTx. The nucleic acid probes of the present invention may be prepared by a variety of techniques known to those skilled in the art, including, without limitation, the following: restriction enzyme digestion of GLUTx nucleic acid; and automated synthesis of oligonucleotides having sequences which correspond to selected portions of the nucleotide sequence of the GLUTx nucleic acid, using commercially-available oligonucleotide synthesizers such as the Applied Biosystems Model 392 DNA/RNA synthesizer.

The nucleic acid probes used in the present invention may be DNA or RNA, and may vary in length from about 8 nucleotides to the entire length of the GLUTx nucleic acid. The GLUTx nucleic acid used in the probes may be derived from mammalian GLUTx. The nucleotide sequence for human GLUTx is known (5, 6). Using this sequence as a probe, the skilled artisan could readily clone corresponding GLUTx cDNA from other species. In addition, the nucleic acid probes of the present invention may be labeled with one or more detectable markers. Labeling of the nucleic acid probes may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as $^{35}S$, $^{32}P$, or $^{3}H$, or nonradioactive labels, such as biotin, fluorescein (FITC), acridine, cholesterol, or carboxy-X-rhodamine (ROX). Combinations of two or more nucleic acid probes (or primers), corresponding to different or overlapping regions of the GLUTx nucleic acid, also may be used to assay a diagnostic sample for GLUTX expression, using, for example, PCR or RT-PCR.

The detection of GLUTx expression in the method of the present invention may be followed by an assay to measure or quantify the extent of GLUTx expression in a diagnostic sample of a subject. Such assays are well known to one of skill in the art, and may include immunohistochemistry/immunocytochemistry, flow cytometry, mass spectroscopy, Western blot analysis, or an ELISA for measuring amounts of GLUTx protein. For example, to use an immunohistochemistry assay, histological (paraffin-embedded) sections of tissue may be placed on slides, and then incubated with an antibody against GLUTx. The slides then may be incubated with a second antibody (against the primary antibody), which is tagged to a dye or other colorimetric system (e.g., a fluorochrome, a radioactive agent, or an agent having high electron-scanning capacity), to permit visualization of GLUTx that is present in the sections.

It is contemplated that the diagnostic sample in the present invention frequently will be assayed for GLUTx expression not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for GLUTx expression.

It is also within the confines of the present invention to use detected levels of GLUTx expression in an assayed diagnostic sample as a clinical or pathologic staging tool. For example, as disclosed herein, GLUTx levels detected by immunoblot analysis in non-metastatic rat mammary adenocarcinoma cells (MTC cells) were significantly (three-fold) lower than those detected in metastatic rat mammary adenocarcinoma cells (MTLn3 cells). Accordingly, detected levels of GLUTx expression in an assayed diagnostic sample may be used to determine the grade or stage of the defect in cell proliferation found in a tissue or bodily fluid of the subject or patient. In addition, detected levels of GLUTx expression in an assayed diagnostic sample may be used to determine whether any treatment method is appropriate for a particular subject or patient who has a defect in cell proliferation, including any of the treatment methods disclosed herein.

The present invention further provides a method for assessing the efficacy of therapy to treat a defect in cell proliferation in a subject or patient who has undergone or is undergoing treatment for a defect in cell proliferation. The method of the present invention comprises assaying a diagnostic sample of the subject or patient for GLUTx expression, wherein detection of GLUTx expression elevated above normal in the diagnostic sample is indicative of a need to continue therapy to treat the defect in cell proliferation, and normal GLUTx expression in the diagnostic sample is indicative of successful therapy.

In accordance with the method of the present invention, the defect in cell proliferation may be any of those described above, including pre-neoplastic lesions and neoplasms, such as mammary adenocarcinomas and endometrial adenocarcinomas. Preferably, the defect in cell proliferation of the present invention is an adenocarcinoma; more preferably, the defect in cell proliferation is mammary adenocarcinoma or endometrial adenocarcinoma. The diagnostic sample may be a tissue or a bodily fluid, as described above. The diagnostic sample may be assayed for expression of GLUTx in vitro or in vivo. In addition, the diagnostic sample may be assayed for expression of GLUTx using all of the various assays and methods of detection and quantification described above. This method of the present invention provides a means for monitoring the effectiveness of therapy to treat a defect in cell proliferation by permitting the periodic assessment of levels of GLUTx expression in a diagnostic sample taken from a subject or patient.

According to the method of the present invention, a diagnostic sample of a subject or patient may be assayed, and levels of GLUTx expression may be assessed, at any time following the initiation of therapy to treat a defect in cell proliferation. For example, levels of GLUTx expression may be assessed while the subject or patient is still undergoing treatment for a defect in cell proliferation. Where GLUTx expression continues to be detected at levels elevated above normal in an assayed diagnostic sample of the subject or patient, a physician may choose to continue with the subject's or patient's treatment for the defect in cell proliferation. Where levels of GLUTx expression in an assayed diagnostic sample of the subject or patient decrease through successive assessments, it may be an indication that the treatment for a defect in cell proliferation is working, and that treatment doses could be decreased or even ceased. Where levels of GLUTx in an assayed diagnostic sample of the subject or patient do not rapidly decrease through successive assessments, it may be an indication that the treatment for a defect in cell proliferation is not working, and that treatment doses could be increased. Where GLUTx expression is no longer detected at levels elevated above normal in an assayed diagnostic sample of a subject or patient, a physician may conclude that the treatment for a defect in cell proliferation has been successful, and that such treatment may cease.

It is also within the confines of the present invention to assess levels of GLUTx expression following completion of the subject's or patient's treatment for a defect in cell proliferation, in order to determine whether the defect in cell proliferation has recurred in the subject or patient. Accordingly, an assessment of levels of GLUTx expression in an assayed diagnostic sample may provide a convenient way to conduct follow-ups of patients with defects in cell proliferation. Furthermore, as described above, it is within the confines of the present invention to use assessed levels of GLUTx expression in an assayed diagnostic sample as a clinical or pathologic staging tool, as a means of determining the extent of the defect in cell proliferation in the subject or patient, and as a means of ascertaining appropriate treatment options.

It is contemplated that the diagnostic sample of the present invention frequently will be assayed for GLUTx expression not by the subject or patient, nor by his/her consulting physician, but by a laboratory technician or other clinician. Accordingly, this method of the present invention further comprises providing to a subject's or patient's consulting physician a report of the results obtained upon assaying a diagnostic sample of the subject or patient for GLUTx expression.

In general, a correlation exists between tumor burden and the survival of a patient who has cancer. The mortality from cancer can be significantly reduced if tumors are found and treated at an early stage. As disclosed herein, GLUTx levels detected by immunoblot analysis in non-metastatic rat mammary adenocarcinoma cells (MTC cells) (favorable prognosis) were significantly (three-fold) lower than those detected in metastatic rat mammary adenocarcinoma cells (MTLn3 cells) (unfavorable prognosis). Accordingly, overexpression of GLUTx correlates with the staging of the neoplastic lesion and the prognosis of the patient.

In view of the foregoing, it is also contemplated in the present invention that assaying a diagnostic sample for GLUTx expression may be a useful means of providing information concerning the prognosis of a subject or patient who has a defect in cell proliferation. Accordingly, the present invention further provides a method for assessing the prognosis of a subject who has a defect in cell proliferation, comprising assaying a diagnostic sample of the subject for GLUTx expression, wherein the subject's prognosis improves with a decrease in GLUTx expression in the diagnostic sample, the subject's prognosis worsens with an increase in GLUTx expression in the diagnostic sample, the subject's prognosis is favorable at low levels of GLUTx expression in the diagnostic sample, and the subject's prognosis is unfavorable at high levels of GLUTx expression in the diagnostic sample.

In accordance with the method of the present invention, the defect in cell proliferation may be any of those described above, including pre-neoplastic lesions and neoplasms, such as mammary adenocarcinomas and endometrial adenocarcinomas. Preferably, the defect in cell proliferation of the present invention is an adenocarcinoma; more preferably, the defect in cell proliferation is mammary adenocarcinoma or endometrial adenocarcinoma. The diagnostic sample may be a tissue or a bodily fluid, as described above. The diagnostic sample may be assayed in vitro or in vivo. In addition, the diagnostic sample may be assayed using all of the various assays and detection and quantification methods described above. This method of the present invention provides a means for determining the prognosis of a subject or patient diagnosed with a defect in cell proliferation based upon the level of GLUTx expression in an assayed diagnostic sample of the subject or patient.

According to the method of the present invention, a diagnostic sample of a subject or patient may be assayed, and levels of GLUTx expression may be assessed, at any time during or following the diagnosis of a defect in cell proliferation in the subject or patient. For example, levels of GLUTx expression in an assayed diagnostic sample may be assessed before the subject or patient undergoes treatment for a defect in cell proliferation, in order to determine the subject's or patient's initial prognosis. Additionally, levels of GLUTx expression in an assayed diagnostic sample may be assessed while the subject or patient is undergoing treatment for a defect in cell proliferation, in order to determine whether the subject's or patient's prognosis has become more or less favorable.

Where levels of GLUTx expression detected in an assayed diagnostic sample of the subject or patient are, or continue to remain, significantly high, a physician may conclude that the subject's or patient's prognosis is unfavorable. Where levels of GLUTx expression in an assayed diagnostic sample of the subject or patient decrease through successive assessments, it may be an indication that the subject's or patient's prognosis is improving. Where levels of GLUTx in an assayed diagnostic sample of the subject or patient do not decrease significantly through successive assessments, it may be an indication that the subject's or patient's prognosis is not improving. Where GLUTx expression is low, or is no longer detected in an assayed diagnostic sample of the subject or patient, a physician may conclude that the subject's or patient's prognosis is favorable.

It is contemplated that the diagnostic sample of the present invention frequently will be assayed for GLUTx expression not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for GLUTx expression.

The discovery that GLUTx can be detected at levels elevated above normal in tumors of subjects suffering from cancer and other defects in cell proliferation provides a means of identifying patients with defects in cell proliferation, and presents the potential for commercial application in the form of a test for the diagnosis of defects in cell proliferation. The development of such a test would provide general screening procedures. Such procedures could assist in the early detection and diagnosis of such cancers, and could provide a method for the follow-up of patients in whom GLUTx expression has been detected at levels elevated above normal. Accordingly, the present invention further provides a kit for use as an assay of defects in cell proliferation, comprising an agent reactive with GLUTx. The agent may be any of those described above, and may be used in any of the above-described assays or methods for detecting or quantifying GLUTx expression.

The present invention is also directed to a method for treating a defect in cell proliferation in a subject in need of treatment thereof. As used herein, the "subject" is a mammal, including, without limitation, a cow, dog, human, monkey, mouse, pig, or rat, as described above. Preferably, the subject is a human. Examples of defects in cell proliferation which may be treated by the method of the present invention include, without limitation, pre-neoplastic lesions and neoplasms, such as mammary adenocarcinomas and endometrial adenocarcinomas, as described above. Preferably, the defect in cell proliferation of the present invention is an adenocarcinoma; more preferably, the defect in cell proliferation is mammary adenocarcinoma or endometrial adenocarcinoma.

The method of the present invention comprises inhibiting GLUTx. GLUTx may be inhibited in a subject by disabling, disrupting, or inactivating the function of GLUTx in a tumor or other defect in cell proliferation in the subject, or by diminishing the amount of GLUTx in a tumor or other defect in cell proliferation in the subject. Furthermore, GLUTx may be inhibited by targeting GLUTx directly, or by targeting a molecule that modulates or regulates GLUTx function or GLUTx levels. GLUTx inhibitors provide novel and valuable tools for treating defects in cell proliferation. Because GLUTx is generally not expressed at significantly high levels in nondiseased subjects, apart from cells of the male reproductive organs (as disclosed below), inhibition of GLUTx should have a therapeutic effect without resulting in harmful or deleterious side-effects which may frequently accompany therapies using other antineoplastic drugs or radiation.

In one embodiment of the present invention, GLUTx is inhibited by administering a GLUTx inhibitor to a subject who has a defect in cell proliferation. As used herein, "a GLUTx inhibitor" shall include a protein; a polypeptide; a peptide; a nucleic acid, including DNA, RNA, a ribozyme specific for GLUTx, and an oligonucleotide antisense to GLUTx; an antibody, including a monoclonal and a polyclonal antibody, as described above, an antibody specific for GLUTx exofacial epitopes, and an antibody specific for other GLUTx epitopes; a Fab fragment, as described above; a F(ab')$_2$ fragment, as described above; a molecule; a compound; an antibiotic; a drug; and any combinations thereof. Additionally, the GLUTx inhibitor of the present invention may be an agent reactive with GLUTx protein or nucleic acid, as defined above.

Oligonucleotides antisense to GLUTx may be designed based on the nucleotide sequence of GLUTx (Genbank accession number XM_011828). For example, a partial sequence of the GLUTx nucleotide sequence (generally, 18–20 base pairs), or a variation sequence thereof, may be selected for the design of an antisense oligonucleotide. This portion of the GLUTx nucleotide sequence may be within the 5' domain. A nucleotide sequence complementary to the selected partial sequence of the GLUTx gene, or the selected variation sequence, then may be chemically synthesized using one of a variety of techniques known to those skilled in the art, including, without limitation, automated synthesis of oligonucleotides having sequences which correspond to a partial sequence of the GLUTx nucleotide sequence, or a variation sequence thereof, using commercially-available oligonucleotide synthesizers such as the Applied Biosystems Model 392 DNA/RNA synthesizer.

Once the desired antisense oligonucleotide has been prepared, its ability to inhibit GLUTx then may be assayed. For example, the oligonucleotide antisense to GLUTx may be contacted with tumor cells derived from a tumor cell line, such as MTLn3 or MTC, and the levels of GLUTx expression in the cells may be determined using standard techniques, such as Western blot analysis. Alternatively, the antisense oligonucleotide may be delivered to tumor cells derived from a tumor cell line using a liposome vehicle, and the levels of GLUTX expression in the cells then may be determined using standard techniques, such as Western blot analysis. Where the level of GLUTx expression in tumor cells is reduced in the presence of the designed antisense oligonucleotide, it may be concluded that the oligonucleotide could be a useful GLUTx inhibitor.

It is within the confines of the present invention that an oligonucleotide antisense to GLUTx may be linked to another agent, such as an antineoplastic drug or a ribozyme, in order to increase the effectiveness of the treatment, to increase the efficacy of targeting, and/or to increase the efficacy of degradation of GLUTx RNA. Examples of antineoplastic drugs to which the antisense oligonucleotide may be linked include, without limitation, carboplatin, cyclophosphamide, doxorubicin, etoposide, and vincristine. Moreover, oligonucleotide antisense to GLUTx may be prepared using modified bases (e.g., a phosphorothioate) to make the oligonucleotide more stable and better able to withstand degradation.

Agents reactive with GLUTx protein may act as antagonists or GLUTx inhibitors, thereby reducing the activity of GLUTx. Agents that are reactive with the GLUTx nucleic acid may suppress expression of the GLUTx nucleic acid (e.g., by functioning as a repressor). Agents that are reactive with either GLUTx protein or nucleic acid may be identified using standard in vitro assays known in the art, including binding assays. For example, a candidate agent may be contacted with GLUTx protein or nucleic acid, and the ability of the agent to bind to the GLUTx protein or nucleic acid may be assessed using standard techniques.

Additionally, a candidate agent may be contacted with tumor cells derived from a tumor cell line, such as MTLn3 or MTC, and the levels of GLUTx expression in the cells may be determined using standard techniques, such as Western blot analysis. Similarly, a candidate agent may be contacted with tumor cells derived from a tumor cell line, such as MTLn3 or MTC, and the level of GLUTx-binding activity in the cells then may be determined using a cytochalasin B or ATB-BMPA assay (5, 35). Where the level of GLUTx expression or binding activity in tumor cells derived from a tumor cell line, such as MTLn3 or MTC, is reduced in the presence of the candidate agent, it may be concluded that the candidate could be a useful agent that inhibits GLUTx in tumors and other defects in cell proliferation.

Additionally, agents reactive with GLUTx may be detected in a functional assay. For example, glucose uptake by GLUTx inserted in the membrane of a liposome may be measured in the presence of a candidate agent. Where the candidate agent binds to, or inhibits, GLUTx, glucose uptake will decrease or cease. While GLUTx is similar to other glucose transporters, it does possess many unique sequences in the glucose-sensing and glucose-transporting regions. Accordingly, candidate agents that efficiently and specifically inhibit GLUTx activity may be easily detected.

Agents that regulate the expression of GLUTx nucleic acid, including agents that bind to sites that downregulate GLUTx, also may be useful as GLUTx inhibitors in the present invention. Accordingly, the GLUTx inhibitor of the present invention may be a modulator of GLUTx expression. The modulator may be a protein, polypeptide, peptide, nucleic acid (including DNA or RNA), antibody, Fab fragment, $F(ab')_2$ fragment, molecule, compound, antibiotic, drug, or other agent, as defined herein, that terminates or downregulates GLUTx expression. Appropriate modulators of GLUTx expression may be identified by contacting a candidate agent with a cell transformed with a vector comprising the GLUTx nucleic acid, and assessing the effect of the agent on expression of GLUTx nucleic acid.

Once the candidate agent or modulator of the present invention has been screened, and has been determined to have a suitable inhibitory effect on GLUTx (i.e., it is reactive with GLUTx, it binds GLUTx, or it otherwise inactivates GLUTx), it may be evaluated for its effect on tumors and other defects in cell proliferation. In particular, the candidate agent or modulator may be assessed for its ability to act as an inhibitor to cell division or to otherwise function as an appropriate tumor-suppressing agent. It is expected that the GLUTx inhibitor of the present invention will be useful in treating defects in cell proliferation, including those disclosed herein, and in creating disease models.

In the method of the present invention, a GLUTx inhibitor is administered to a subject who has a defect in cell proliferation in an amount effective to treat the defect in cell proliferation in the subject. As used herein, the phrase "effective to treat the defect in cell proliferation" means effective to ameliorate or minimize the clinical impairment or symptoms resulting from the defect in cell proliferation. For example, the clinical impairment or symptoms of the defect in cell proliferation may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the maturation and proliferation of cells in the defect in cell proliferation.

The amount of GLUTx inhibitor effective to treat a defect in cell proliferation in a subject in need of treatment thereof will vary depending on the particular factors of each case, including the type of defect in cell proliferation, the stage of the neoplastic lesion, the subject's weight, the severity of the subject's condition, and the method of administration. These amounts can be readily determined by the skilled artisan.

In the method of the present invention, the GLUTx inhibitor may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. Preferably, the GLUTx inhibitor of the present invention is administered parenterally, by intravenous or subcutaneous injection.

For oral administration, the formulation of the GLUTx inhibitor may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the GLUTx inhibitor may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. The formulation may be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

For transdermal administration, the GLUTx inhibitor may be combined with skin penetration enhancers, such as propylene glycol, polyethylene glycol, isopropanol, ethanol, oleic acid, N-methylpyrrolidone, and the like, which increase the permeability of the skin to the GLUTx inhibitor, and permit the GLUTx inhibitor to penetrate through the skin and into the bloodstream. The GLUTx inhibitor/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The GLUTx inhibitor may be administered transdermally, at or near the site on the subject where the defect in cell proliferation is localized. Alternatively, GLUTX inhibitor may be administered transdermally at a site other than the affected area, in order to achieve systemic administration.

The GLUTx inhibitor of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the GLUTx inhibitor.

In accordance with the methods of the present invention, where the GLUTx inhibitor is a protein, the GLUTx inhibitor protein may be administered to a subject by introducing to the subject the GLUTx inhibitor protein itself, or by introducing to the subject a nucleic acid encoding the GLUTx inhibitor in a manner permitting expression of the GLUTx inhibitor protein. The GLUTx inhibitor protein, and other GLUTx inhibitors, may be introduced to a subject by known techniques used for the introduction of proteins and other drugs, including, for example, injection and transfusion. Where a defect in cell proliferation is localized to a particular portion of the body of the subject, it may be desirable to introduce the GLUTx inhibitor directly to that area by injection or by some other means (e.g., by introducing GLUTx inhibitor into the blood or another bodily fluid). The amount of GLUTx inhibitor to be used is an amount effective to treat a defect in cell proliferation in the subject, as defined above, and may be readily determined by the skilled artisan.

In the method of the present invention, where the GLUTx inhibitor is a protein, the GLUTx inhibitor also may be introduced to the subject by introducing into a sufficient number of cells of the subject a nucleic acid encoding the GLUTx inhibitor, in a manner permitting expression of the GLUTx inhibitor protein. The amount of nucleic acid encoding GLUTx inhibitor is an amount that will produce GLUTx inhibitor protein in an amount effective to treat a defect in cell proliferation, as defined above, in the subject. This amount may be readily determined by the skilled artisan.

Nucleic acid encoding a GLUTx inhibitor, as well as any antisense oligonucleotide or other nucleotide inhibitor of GLUTx, may be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, naked DNA transfer, and any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus.

It is also within the confines of the present invention that a nucleic acid encoding a GLUTx inhibitor may be introduced into suitable cells in vitro, using conventional procedures, to achieve expression of the GLUTx inhibitor in the cells. Cells expressing the GLUTx inhibitor then may be introduced into a subject to treat a defect in cell proliferation in vivo. In such an ex vivo gene therapy approach, the cells are preferably removed from the subject, subjected to DNA techniques to incorporate nucleic acid encoding the GLUTx inhibitor, and then reintroduced into the subject.

Furthermore, it is within the confines of the present invention that the GLUTx inhibitor of the present invention may be administered to a subject who has a defect in cell proliferation, either alone or in combination with one or more antineoplastic drugs used to treat defects in cell proliferation. Examples of antineoplastic drugs with which the GLUTx inhibitor may be combined include, without limitation, carboplatin, cyclophosphamide, doxorubicin, etoposide, and vincristine.

Additionally, it is within the confines of the present invention that a formulation of a GLUTx inhibitor may be further associated with a pharmaceutically-acceptable carrier, thereby comprising a pharmaceutical composition. The pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical art. For example, a GLUTX inhibitor may be brought into association with a carrier or diluent, as a suspension or solution. Optionally, one or more accessory ingredients (e.g., buffers, flavoring agents, surface active agents or surfactants, and the like) also may be added. The choice of carrier will depend upon the route of administration. The pharmaceutical composition would be useful for administering the GLUTx inhibitor of the present invention to a subject to treat a defect in cell proliferation. The GLUTx inhibitor is provided in an amount that is effective to treat a defect in cell proliferation in the subject. That amount may be readily determined by the skilled artisan, as described above.

As described above, overexpression of GLUTx may be associated with defects in cell proliferation, while deficient expression of GLUTx may contribute to problems coincident with ischemia, male and female infertility, and other conditions of high stress where nutrients and/or oxygen often are lacking. Accordingly, the present invention further provides a method for treating ischemia in a subject in need of treatment thereof, comprising administering to the subject an amount of GLUTx effective to treat the ischemia in the subject. As defined above, "GLUTx" includes both a GLUTx protein and a "GLUTx analogue". As used herein, "ischemia" refers herein to a deficiency in blood in a particular part of the body, due to functional constriction or actual obstruction of a blood vessel. Examples of ischemia include, without limitation, bone infarction, bone ischemia, bowel infarction, cerebellar infarction, cerebral infarction, cerebral ischemia, hepatic infarction, intestinal ischemia, ischemic colitis, ischemic heart disease, myocardial infarction, myocardial ischemia, pulmonary infarction, renal infarction, spinal infarction, splenic infarction, and stroke. The subject is preferably a mammal (e.g., a cow, dog, human, monkey, mouse, pig, or rat), as described above, and is more preferably a human.

In the method of the present invention, GLUTx is administered to a subject who has ischemia in an amount effective to treat the ischemia in the subject. As used herein, the phrase "effective to treat the ischemia" means effective to ameliorate or minimize the clinical impairment or symptoms resulting from the ischemia. For example, where the ischemia is ischemic stroke, the clinical impairment or symptoms of the stroke may be ameliorated or minimized by diminishing any aphasia, atrial fibrillation, coma, convulsive seizures, embolism, headache, hemorrhage, hypertension, impaired consciousness, infarction, mental deterioration, pain, stupor, or thrombosis suffered by the subject.

The amount of GLUTx effective to treat ischemia in a subject in need of treatment thereof will vary depending on the particular factors of each case, including the type of ischemia, the subject's weight, the severity of the subject's condition, and the method of administration. These amounts can be readily determined by the skilled artisan.

In accordance with the methods of the present invention, GLUTx may be administered to a subject by introducing into target cells of the subject the GLUTx protein itself, or by introducing into target cells of the subject a nucleic acid encoding GLUTx in a manner permitting expression of GLUTx protein. Target cells include all cells of an ischemic organ or tissue in the subject. Examples of target cells include, without limitation, cells of the bone, bowel, brain, colon, heart, intestines, kidney, liver, lungs, spine, and spleen. Target cells for introduction of the GLUTx protein or nucleic acid may be detected in organs or tissue of the subject by standard detection methods readily determined from the known art, including, without limitation, immunological techniques (e.g., immunohistochemical staining), fluorescence imaging techniques, and microscopic techniques. GLUTx protein or nucleic acid may be administered to a human or animal subject by known procedures, including all modes of administration described above.

GLUTx protein may be introduced into cells of the subject either in vitro or in vivo, by known techniques used for the introduction of proteins into cells (e.g., by means of micro-encapsulated preparations, such as liposomes). The amount of GLUTx protein to be used is an amount effective to treat the ischemia, as defined above, and may be readily determined by the skilled artisan.

For introduction of GLUTx protein by way of liposome delivery, liposomal vesicles may be prepared by various methods known in the art, and liposome compositions may be prepared using any one of a variety of conventional techniques for liposome preparation known to those skilled in the art. Examples of such methods and techniques include, without limitation, chelate dialysis, extrusion (with or without freeze-thaw), French press, homogenization, microemulsification, reverse phase-evaporation, simple freeze-thaw, solvent dialysis, solvent infusion, solvent vaporization, sonication, and spontaneous formation.

Preparation of the liposomes may be carried out in a solution, such as an aqueous saline solution, aqueous phosphate buffer solution, or sterile water. Liposome compositions also may be prepared by various processes involving shaking or vortexing. GLUTx protein may be incorporated into the liposome, and the liposome containing GLUTx then may be fused with a cell, in accordance with known methods of fusion of liposomes to cell membranes, such that the GLUTx protein is delivered into the cell cytosol.

In the method of the present invention, GLUTx also may be administered to a subject by introducing into a sufficient number of target cells of the subject a nucleic acid encoding GLUTx, in a manner permitting expression of GLUTx. The nucleic acid may be introduced using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus. The amount of nucleic acid encoding GLUTx to be used is an amount that will express GLUTx protein in an amount effective to treat ischemia in the subject, as defined above. These amounts may be readily determined by the skilled artisan.

It is also within the confines of the present invention that a nucleic acid encoding GLUTX may be introduced into suitable cells in vitro, using conventional procedures, to achieve expression of GLUTx protein in the cells. Cells expressing GLUTx then may be introduced into a subject to treat ischemia in vivo. In such ex vivo gene therapy approaches, the cells are preferably removed from the subject, subjected to DNA techniques to incorporate nucleic acid encoding GLUTx, and then reintroduced into the subject.

Agents that are reactive with the GLUTx nucleic acid may enhance expression of the GLUTx nucleic acid (e.g., by functioning as a transcription factor, an activator, or a repressor that binds to silencer sites and thereby prevents activator binding or transcription), and may be useful in the present invention. Other agents that regulate the expression of GLUTx nucleic acid, including agents that bind to enhancer sites that upregulate GLUTx, also may be useful in the present invention. Therefore, modulators of GLUTx expression also may be useful in the present invention.

Accordingly, the present invention further provides a method for treating ischemia in a subject in need of treatment thereof, comprising administering to the subject an amount of a GLUTx modulator effective to treat the ischemia in the subject. As defined above, "GLUTx" includes both a GLUTx protein and a "GLUTx analogue". The ischemia may be any of those described above. The subject is preferably a mammal (e.g., a cow, dog, human, monkey, mouse, pig, or rat), as described above, and is more preferably a human.

The modulator of the present invention may be a protein, polypeptide, peptide, nucleic acid (including DNA or RNA), antibody, Fab fragment, $F(ab')_2$ fragment, molecule, compound, antibiotic, drug, or other agent, as defined herein, that enhances or upregulates GLUTX expression. Appropriate modulators of GLUTx expression may be identified by contacting a candidate agent with a cell transformed with a vector comprising the GLUTx nucleic acid, and assessing the effect of the agent on expression of GLUTx nucleic acid.

In the method of the present invention, a modulator of GLUTx expression is administered to a subject who has ischemia in an amount effective to treat the ischemia in the subject, as defined above. The amount of a modulator of GLUTx expression effective to treat ischemia in a subject in need of treatment thereof will vary, depending on the particular factors of each case, including the type of ischemia, the subject's weight, the severity of the subject's condition, and the method of administration. These amounts can be readily determined by the skilled artisan. The modulator of GLUTx expression may be administered to a subject by introducing the modulator into target cells of the subject, in accordance with any of the modes described herein for administering or introducing nucleic acids and proteins. The target cells include any of those described above.

As described above, overexpression of GLUTx may be associated with defects in cell proliferation, while deficient expression of GLUTx may contribute to problems coincident with ischemia, male and female infertility, and other conditions of high stress where nutrients and/or oxygen often are lacking. Accordingly, the present invention further provides a method of treating infertility in a subject in need of treatment thereof, comprising administering to the subject an amount of GLUTx effective to treat the infertility. As defined above, "GLUTx" includes both a GLUTx protein and a "GLUTx analogue". As used herein, "infertility" refers herein to a diminished capacity to produce offspring. Examples of infertility include, without limitation, azoospermia; genetic disorders associated with defective spermatogenesis (e.g., Klinefelter's syndrome and gonadal dysgenesis); oligospermia, varicocele, and other sperm disorders relating to low sperm counts, sperm motility, and sperm morphology; and ovulatory dysfunction (e.g., polycystic ovary syndrome (PCOS) or chronic anovulation). The subject may be a human or a domestic or commercial animal (e.g., a cow, dog, horse, monkey, mouse, pig, or rat). Furthermore, the subject may be either male or female. Preferably, the subject is a mammal. More preferably, the subject is a human.

In the method of the present invention, GLUTx is administered to a subject who has infertility in an amount effective to treat the infertility in the subject. As used herein, the phrase "effective to treat the infertility" means effective to ameliorate or minimize the clinical impairment or symptoms resulting from the infertility. For example, where the infertility is defective spermatogenesis, the clinical impairment or symptoms resulting from the infertility may be ameliorated or minimized by increasing spermatogenesis and elevating the sperm count in the subject. The amount of GLUTx effective to treat infertility in a subject in need of treatment thereof will vary depending on the particular factors of each case, including the type of infertility, the subject's weight, the severity of the subject's condition, and the method of administration. These amounts can be readily determined by the skilled artisan.

In accordance with the methods of the present invention, GLUTx may be administered to a subject by introducing into cells of the subject the GLUTx protein itself, or by introducing into cells of the subject a nucleic acid encoding GLUTx in a manner permitting expression of GLUTx protein. Where GLUTx is administered to a subject to treat infertility, the cells of the subject into which GLUTx may be introduced include any cells of the reproductive organs of the subject, including Sertoli cells, Leydig cells, epithelial cells of the epididymis, granulosa cells, thecal cells, interstitial cells that are precursors to thecal cells, and epithelial cells lining the oviduct. GLUTx protein or nucleic acid may be administered to a human or animal subject by known procedures, including all modes of administration described above. Target cells for introduction of the GLUTx protein or nucleic acid may be detected in organs or tissue of the subject by standard detection methods readily determined from the known art, including, without limitation, immunological techniques (e.g., immunohistochemical staining), fluorescence imaging techniques, and microscopic techniques.

GLUTx protein may be introduced into cells of the subject either in vitro or in vivo, by known techniques used for the introduction of proteins into cells (e.g., by means of micro-encapsulated preparations, such as liposomes). The amount of GLUTx protein to be used is an amount effective to treat the infertility, as defined above, and may be readily determined by the skilled artisan.

For introduction of GLUTx protein by way of liposome delivery, liposomal vesicles may be prepared by various methods known in the art, and liposome compositions may be prepared using any one of a variety of conventional techniques for liposome preparation known to those skilled in the art. Examples of such methods and techniques include, without limitation, chelate dialysis, extrusion (with or without freeze-thaw), French press, homogenization, microemulsification, reverse phase evaporation, simple freeze-thaw, solvent dialysis, solvent infusion, solvent vaporization, sonication, and spontaneous formation.

Preparation of the liposomes may be carried out in a solution, such as an aqueous saline solution, aqueous phosphate buffer solution, or sterile water. Liposome compositions also may be prepared by various processes involving shaking or vortexing. GLUTx protein may be incorporated into the liposome, and the liposome containing GLUTx then may be fused with a cell, in accordance with known methods of fusion of liposomes to cell membranes, such that the GLUTx protein is delivered into the cell cytosol.

In the method of the present invention, GLUTx also may be administered to a subject by introducing into a sufficient number of cells of the subject a nucleic acid encoding GLUTx, in a manner permitting expression of GLUTx. The nucleic acid may be introduced using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semliki Forest virus, cytomegalovirus, and vaccinia virus. The amount of nucleic acid encoding GLUTx to be used is an amount that will express GLUTx protein in an amount effective to treat infertility in the subject, as defined above. These amounts may be readily determined by the skilled artisan.

It is also within the confines of the present invention that a nucleic acid encoding GLUTx may be introduced into suitable cells in vitro, using conventional procedures, to achieve expression in the cells of GLUTx protein. Cells expressing GLUTx then may be introduced into a subject to treat infertility in vivo. In such ex vivo gene therapy approaches, the cells are preferably removed from the subject, subjected to DNA techniques to incorporate nucleic acid encoding GLUTx, and then reintroduced into the subject.

Agents that are reactive with the GLUTx nucleic acid may enhance expression of the GLUTx nucleic acid (e.g., by functioning as a transcription factor, an activator, or a repressor that binds to silencer sites and thereby prevents activator binding or transcription), and may be useful in the present invention. Other agents that regulate the expression of GLUTx nucleic acid, including agents that bind to enhancer sites that upregulate GLUTx, also may be useful in the present invention. Therefore, modulators of GLUTx expression also may be useful in the present invention.

Accordingly, the present invention further provides a method for treating infertility in a subject in need of treatment thereof, comprising administering to the subject an amount of a GLUTx modulator effective to treat the infertility in the subject. As defined above, "GLUTx" includes both a GLUTx protein and a "GLUTx analogue". The infertility may be any of those described above. The subject is preferably a mammal (e.g., a cow, dog, human, monkey, mouse, pig, or rat), as described above, and is more preferably a human.

The modulator of the present invention may be a protein, polypeptide, peptide, nucleic acid (including DNA or RNA), antibody, Fab fragment, F(ab')$_2$ fragment, molecule, compound, antibiotic, drug, or other agent, as defined herein, that enhances or upregulates GLUTx expression. Appropriate modulators of GLUTx expression may be identified by contacting a candidate agent with a cell transformed with a vector comprising the GLUTx nucleic acid, and assessing the effect of the agent on expression of GLUTx nucleic acid.

In the method of the present invention, a modulator of GLUTx expression is administered to a subject who has infertility in an amount effective to treat the infertility in the subject, as defined above. The amount of a modulator of GLUTx expression effective to treat infertility in a subject in need of treatment thereof will vary, depending on the particular factors of each case, including the type of infertility, the subject's weight, the severity of the subject's condition, and the method of administration. These amounts can be readily determined by the skilled artisan. The modulator of GLUTx expression may be administered to a subject by introducing the modulator into target cells of the subject, in accordance with any of the modes described herein for administering or introducing nucleic acids and proteins. The target cells include any of those described above. Accordingly, modulators of GLUTx expression may be used in the present invention. The modulator may be a protein, polypeptide, peptide, nucleic acid (including DNA or RNA), antibody, Fab fragment, F(ab')$_2$ fragment, molecule, compound, antibiotic, drug, or other agent, as defined herein, that enhances or upregulates GLUTx expression. Appropriate modulators of GLUTx expression may be identified by contacting a candidate agent with a cell transformed with a vector comprising the GLUTx nucleic acid, and assessing the effect of the agent on expression of GLUTx nucleic acid.

The present invention is described in the following Experimental Details section, which is set forth to aid in the understanding of the invention, and should not be construed to limit in any way the scope of the invention as defined in the claims which follow thereafter.

Experimental Details

1. Introduction

GLUT4, the insulin-sensitive glucose transporter, is both the major glucose transporter in the muscle, heart, and fat (2), and the predominant facilitative glucose transporter expressed in insulin-responsive tissues such as cardiac and skeletal muscle and adipose tissue (2, 19). Under basal conditions, GLUT4 is sequestered from the plasma membrane in a unique intracellular compartment. In response to various stimuli (i.e., insulin, contraction, hypoxia), GLUT4 translocates to the cell surface, and is mostly responsible for the increase in glucose uptake (20–24).

Previously, using stem cell technology, the inventors genetically ablated GLUT4 from the mouse (1). Unexpectedly, GLUT4-null mice were able to maintain normal glycemia with moderate-fed hyperinsulinemia, even though in vitro studies showed the null muscle to be highly insulin resistant (1, 3). Interestingly, the oxidative soleus muscle of female GLUT4-null mice retained a significant insulin-stimulated glucose uptake (3). Furthermore, skeletal muscle of GLUT4-null mice maintained normal levels of high energy phosphate pools (25). However, unlike serum glucose level, fed serum-free fatty acids and fasted ketone body levels were significantly decreased in GLUT4-null mice (1).

Generally, the metabolic profile of GLUT4-null mice resembled that of endurance-trained athletes (e.g., reduced adiposity, cardiac hypertrophy, reduced serum fatty acids, etc.). Surprisingly, the GLUT4-null mice were not diabetic, even though they were insulin resistant. In fact, the soleus muscle took up significant levels of glucose upon insulin stimulation (3).

To ascertain whether the insulin-stimulated glucose uptake measured in female GLUT4-null soleus muscle resulted from altered GLUT1 trafficking, cell surface photolabeling using ATB-BMPA was employed (35). The results of this analysis demonstrated that GLUT1 trafficking and content were unaltered in GLUT4-null soleus under basal and insulin-stimulated conditions. These results strongly suggested that GLUT4-null mice maintained glucose transport into muscle cells at a level sufficient for normal function through a membrane protein (that was not GLUT1). The inventors speculated that the GLUT4-null muscle compensated for its lack of GLUT4 by expressing a novel glucose transporter.

Recently, the inventors and others cloned a novel transporter molecule, GLUTx (4–7). GLUTx (also referred to as GLUTx1 and GLUT8) does transport glucose and other hexoses when expressed in X. laevis oocytes (6). Moreover, GLUTx contains a di-leucine motif retention signal similar to that of GLUT4. Since GLUT4 translocates to the plasma membrane upon insulin stimulation (2), GLUTx also may translocate to the plasma membrane with the proper stimuli. In fact, in the blastocyst, insulin seems to cause GLUTx translocation to the cell membrane (4). The inventors have hypothesized that GLUTx is a sensor of cellular metabolic status, and that it determines the expression of several genes involved in energy production and/or anabolic processes of RNA and fatty acid synthesis.

2. Materials and Methods (i) GLUTx Antibody

A peptide of 11 amino acids, corresponding to the carboxyterminus of GLUTx outside the putative transmembrane domains, was used to generate a GLUTx-specific antibody following immunization of rabbits (7).

(ii) Immunocytochemistry

Immunohistochemistry was performed according to protocols provided by the Dako LSAB (labeled streptoavidin biotin reagents) and Dako EnVision+System (peroxidase, DAB) kits. However, some modifications were made. In brief, tissue on a slide was deparaffinized in xylene, and rehydrated in water. For cells that were processed, the slides or coverslips containing the cells were fixed in 4% paraformaldehyde for 1 h, then washed 4 times in buffered solution (TBS). The slides were placed in 3% $H_2O_2$ for 15 min in a 37° C. water bath to quench endogenous peroxidase activity. Epitope retrieval in paraffin-embedded tissue was achieved by heating the slides to 95° C. in a pre-heated citric acid solution (0.01 M citric acid, 0.01 M sodium citrate; pH 6.0). This temperature was maintained for 15 min in a microwave on high power or in a steam bath. The slides then were cooled. At this point, processing was started for the slides containing fixed cells.

Next, the primary antibody to GLUTx was applied to the slides for 30 min at room temperature (RT). Slides were rinsed in TBS 3 times for 5 min. The slides then were incubated with secondary antibody, as provided in the kit, for 15–20 min at RT. The slides were rinsed well with PBS, and the tertiary reagent (Strep-Avidin or HRP-labeled EnVision polymer) was applied for 15–20 min at RT. The slides then were rinsed well in PBS, and the chromogen solution (containing 3-amino-9-ethylcarbazole (AEC) or 3,3'-diaminobenzidine (DAB)) was applied for 2–5 min to achieve the desired color intensity. Slides were rinsed twice in dd $H_2O$, and then in tap water. The slides then were counterstained with hemotoxylin for 30–60 sec. After rinsing, the slides were rinsed in tap water, dipped 10 times in 1% ammonia water, rinsed again in tap water, and then coverslipped with Dako Glycergel mounting solution.

(iii) Immunoblot Analyses of GLUTx

Immunoblot analyses of GLUTx (FIGS. 1–2, 4–6, and 13) were performed on membrane fractions prepared by methods adapted from Ryder et al. (35). Cardiac and tumor tissues were homogenized in Buffer A (250 mM sucrose, 2 mM EDTA, 40 mM Hepes; pH 7.4), followed by a 10-min centrifugation at 3500 rpm, at a temperature of 4° C. The supernatant then was centrifuged at 9000 rpm for 10 min, at a temperature of 4° C. The resulting supernatant was centrifuged at 227,000× g for 75 min, at a temperature of 4° C. The remaining pellet was dissolved in Buffer B (PBS and 2% Thesit), and left on ice for 30 min to ensure that the pellet had completely dissolved. Homogenates (100 µg of protein) were separated by 10% SDS-PAGE electrophoresis, and transferred to Hybond ECL nitrocellulose (Amersham Inc.). The GLUTx antibody then was used to detect GLUTx expression in total homogenates (100 µg) using ECL reagents (Amersham Inc.).

Membranes were blocked for 30 min in a solution of 5% non-fat dry milk in TBS and 0.05% Tween 20 (TBST), then incubated with GLUTx antibody (1:500 dilution in 5% milk) for 1 h at RT. The membrane was then rinsed in 5% milk for 15 min, and washed 3 times for 5 min in TBST. After blocking again for 30 min at RT in 5% milk, the membrane was incubated in peroxidase-labeled anti-rabbit secondary antibody (1:5000 dilution in 5% milk solution) for 1 h at RT. The membrane was then rinsed again for 10 min in 5% milk, then washed 4 times for 5 min in TBST at RT.

GLUTx was detected using enhanced chemiluminescence reagents (Amersham Pharmacia). In competition studies, an excess of immunizing peptide (36 µg) was added to 3 µl of GLUTx polyclonal immune serum, and incubated for 1 h at 4° C. The competing serum was then used in a 1:500 dilution. Intensities were quantified through the use of a Molecular Dynamics scanning densitometer and compatible software.

(iv) MTLn3 Cells

MTLn3 (metastasizing) rodent breast cancer cells were cloned from a transplantable tumor which was induced by carcinogen treatment of female Fischer 344 rats (36). The MTLn3 cells were grown on slides. in α-MEM media supplemented with 10% fetal calf serum and penicillin/ streptomycin (Gibco). The cells then were stimulated with insulin (500 nM) for 1 h. Immunocytochemistry was performed as described above using the AEC chromogen (FIG. 3). MTLn3 cells also were grown as described above, then seeded onto coverslips at 50% confluency. The cells then were incubated for 4 days with media, media+10 µM BRL49653, or media+40 µM BRL48653. After 4 days, immunocytochemistry was performed, as described above, using the DAB chromogen (FIGS. 3 and 4).

(v) MTC Cells

MTC (non-metastasizing) rodent breast cancer cells were cloned from a transplantable tumor which was induced by carcinogen treatment of female Fischer 344 rats (36). The MTC cells were grown as described above for MTLn3 cells. The MTC cells were exposed either to insulin (500 nM) or hypoxia by replacing a 5% $CO_2$ mixture with 95% $CO_2$ for 1 h. Immunocytochemistry was performed as described above using the AEC chromogen (FIG. 3). MTC cells also were grown as described above, then seeded onto coverslips at 50% confluency. The cells then were incubated for 4 days with media, media+10 µM BRL49653, or media+40 µM BRL48653. After 4 days, immunocytochemistry was performed, as described above, using the DAB chromogen (FIGS. 3 and 4).

(vi) Assessment of GLUTx mRNA in Human Tissue Using RT-PCR

Total RNA was extracted from 100 mg of human vastus lateralis muscle biopsies or normal, dysplastic, or malignant endometrium. For each reverse transcription reaction, 0.5 µg of RNA were used. Reverse transcription was carried out using Gibco BRL Supercript II, as suggested by the manufacturer. Of the total reaction volume (20 µl), 1 µl was used for the subsequent PCR. Complementary DNA was amplified using both GLUTx and β-actin primers. GLUTx primers amplify a 351-bp fragment spanning base pairs 680 to 1030 of the human cDNA. The forward primer is a 21-mer, and the reverse primer is a 20-mer. β-actin primers amplify a 353-bp fragment.

The PCR reaction was prepared by combining the following: 5 µl of 10X PCR buffer (1X final; Gibco BRL), 1.5 µl of 50-mM $MgCl_2$ (1.5 mM final conc.), 1 µl of 10-mM dNTP (0.2 mM each, final conc.), 1 µl each of 20-mM forward and reverse primers (0.4 mM final conc.), 0.5 µl of Platinum Taq DNA Polymerase (Gibco BRL), 1 µl of CDNA template, 0.05-0.1 µl of $^{32}P$ α-dCTP, and autoclaved water to 50 µl. PCR conditions were as follows: initial annealing at 94° C. for 2 min; cycling at 94° C. for 30 sec, 57° C. for 30 sec, and 72° C. for 30 sec, for 30 cycles; and final annealing at 72° C. for 7 min. Reactions for GLUTx and β-actin were carried out separately.

Aliquots of each sample (25 µl) were run on an 8% polyacrylamide gel, at 200 V, for 1 h. Gels were dried under vacuum pressure, at 80° C. for 2 h, exposed for 2 h using a Molecular Dynamics Phosphor screen, and analyzed using Image Quant software. Values for GLUTx were normalized by β-actin.

(vii) Langendorff Perfusion and Contractile Performance

Figure 9:
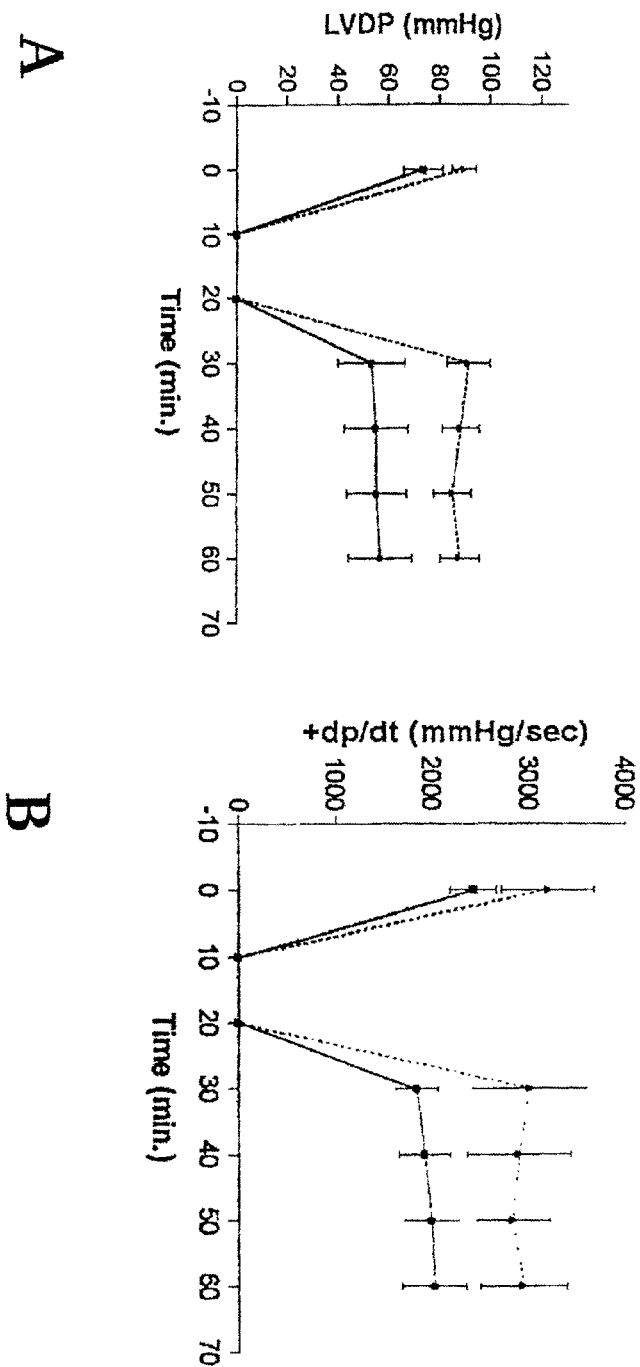
FIG. 9 compares the contractile performance of null hearts with that of control hearts after a period of ischemia followed by reperfusion. The null heart recovered most of its contractile function, while the control heart lost function. Cardiac contractile performance at baseline, during ischemia and reperfusion in GLUT4-null hearts (dashed line-triangles - - ▲- -; n=4), is compared with wild-type (solid line+squares ---■---; n=3) hearts. Panel A shows better recovery of LVDP in GLUT4-null hearts after 20 min of global ischemia and up to 40 min of reperfusion. Panel B shows better recovery of +dP/dt in GLUT4-null hearts, as compared with wild-type control hearts.

Mice 6 weeks of age were given i.p. injections of heparin, and euthanized by cervical dislocation. Hearts were removed and cannulated through the aorta for retrograde Langendorff perfusion (FIG. 9). Briefly, hearts were perfused with buffer (118 mM NaCl, 25 mM $NaHCO_3$, 2 mM $CaCl_2$, 0.2 mM $MgSO_4$, 0.5 mM EDTA, 5.3 mM KCl, 0.5 mM pyruvate), gassed with 95% $O_2$ and 5% $CO_2$, and kept at a temperature of 37° C. and a pressure of 60 mmHg for a 30-min equilibrium period. Subsequently, hearts were subjected to no-flow ischemia for 20 min, followed by 40 min of reperfusion. Heart function was assessed by introducing into the left ventricle a fluid-filled balloon connected to a pressure transducer. Hearts were monitored for left ventricular developed pressure (LVDP), heart rate (HR), dP/dt, and coronary flow through the use of the Ponemah Physiology suite of software.

(viii) Infarct Size Determination

Figure 10:
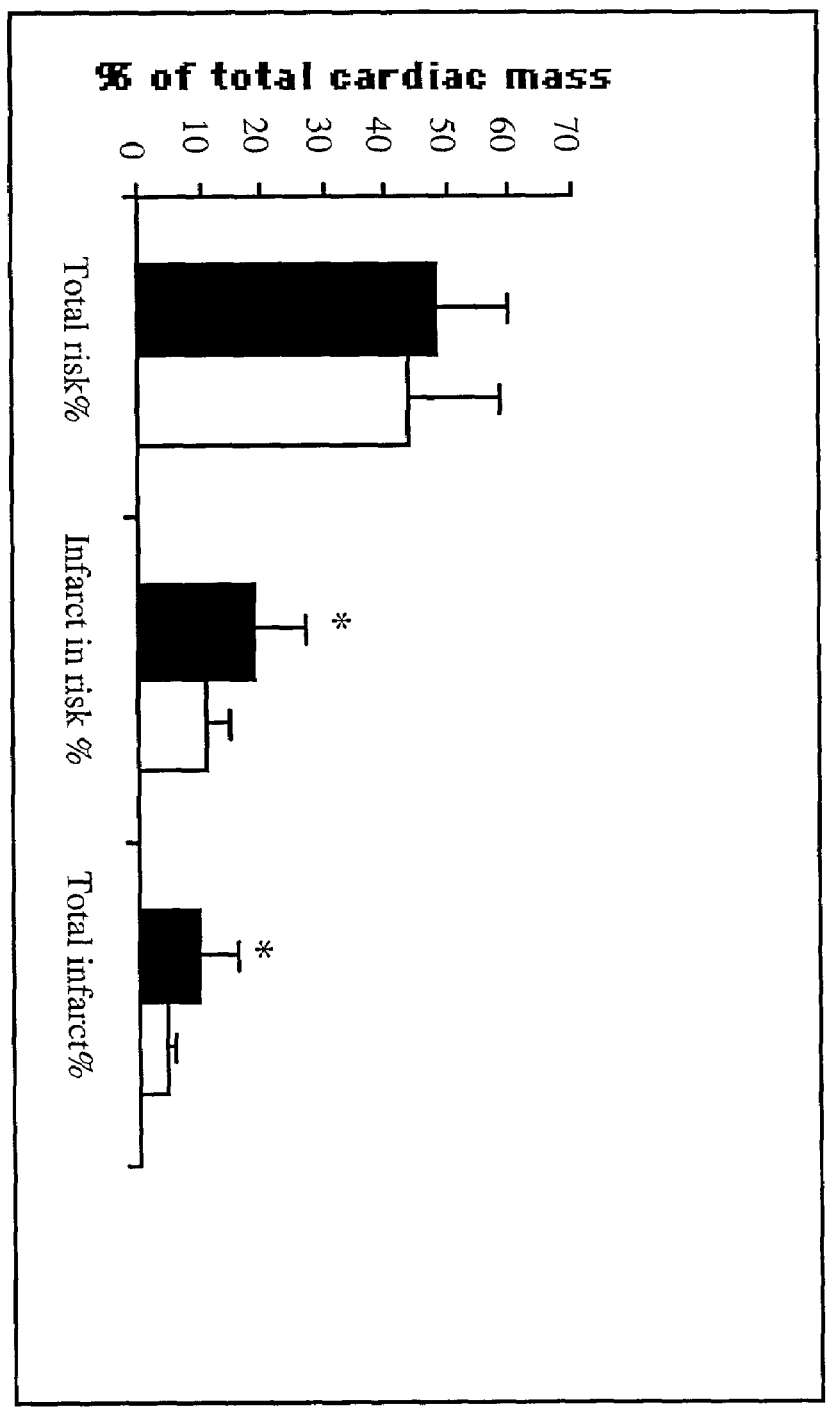
FIG. 10 illustrates the results of studies involving 45 min of in vivo ischemia, followed by 24 h of reperfusion, in 6-week-old mice. GLUT4-null mice showed significantly less infarct within the risk area and significantly less total infarct area. ■=control mice; □=GLUT-4 null mice; *=p<0.05

A surgically-imposed, 45-min coronary artery occlusion in mice was followed by 4- or 24-h reperfusion according to methods described previously (37). After reperfusion, anesthetized mice were sacrificed by cervical dislocation, and their hearts were removed for retrograde perfusion with a phosphate-free Krebs-Henseleit buffer at a temperature of 37° C. and a pressure of 80 mmHg. After an equilibration period, hearts were arrested with 20 mM KCl. The same coronary occlusion was retied with the original suture. The hearts then were perfused with a 5% solution of phthalo blue dye (Heucotech, Fairless Hill, Pa.) in saline, to denote viable tissue. After removal from the cannula, hearts were sectioned into 6 slices and fixed in 10% neutral buffered formalin. After 24 h, the slices were weighed and photographed with a digital camera (Nikon, Coolpix). The photos were analyzed for infarct, risk area, and viable tissue, through the use of ImageJ software (FIG. 10).

(ix) Positron Emission Tomography Scan of the Heart

Figure 7:
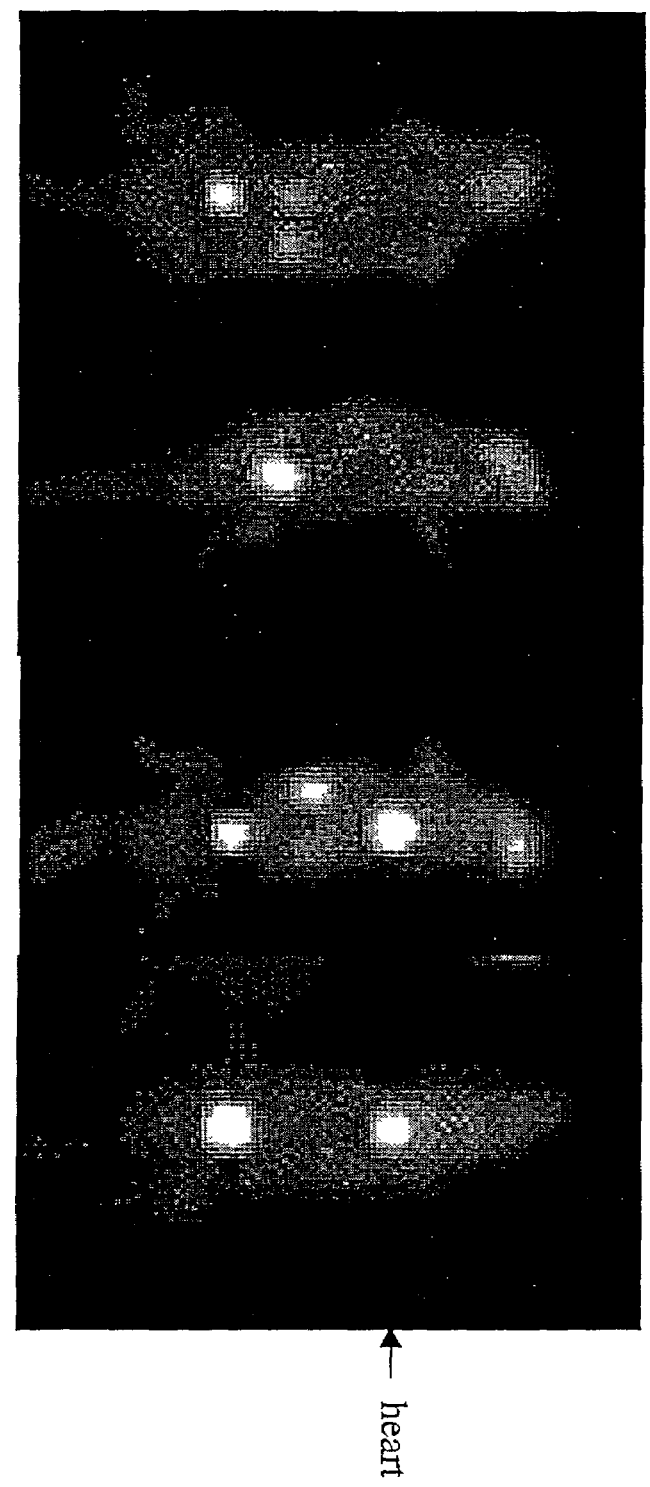
FIG. 7 shows Positron Emission Tomography (PET) images of 18-fluoro-2-deoxyglucose (FDG) uptake into control and null hearts. In the fasted state, FDG was not detected in either the control heart or the null heart. However, 1 h after a 1 g/kg dose of glucose and an 8 unit/kg injection of insulin, more glucose uptake was seen in the null heart than in the control heart.
Figure 8:
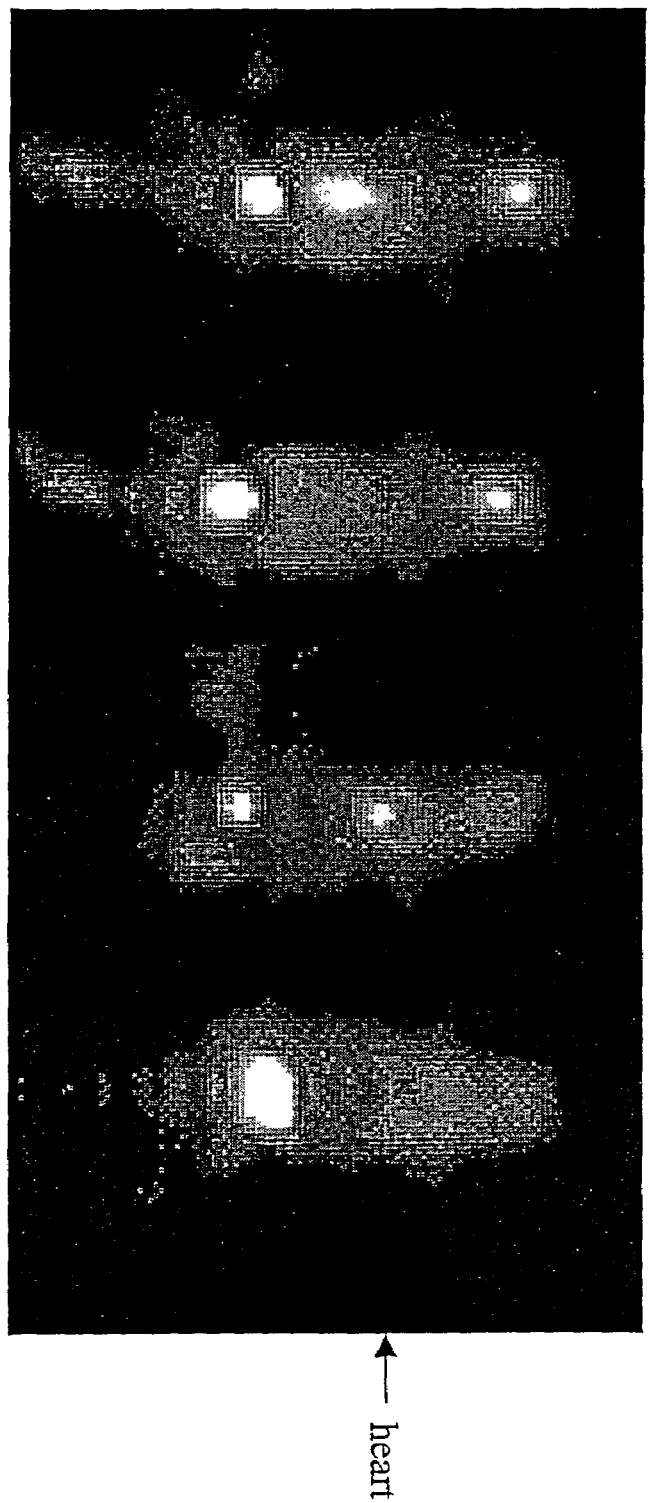
FIG. 8 demonstrates that a PET scan of fed animals, following a short (90-min) stimulation with insulin, identifies significantly more FDG in the null heart than in the control heart.

GLUT4-null mice (male, n=6) and age-matched wild-type (male, n=5) mice were imaged with an ECAT EXACT HR+PET scanner, 40 min after injection of 15 MBq F-18 FDG in the tail vein (FIGS. 7 and 8). Four groups were studied: two insulin groups (GLUT4 null, n=8; wild-type, n=2) that had been pre-treated with 8 units/kg of insulin and 1 g/kg of glucose 1 h before FDG injection, and two fasted control groups (GLUT4-null, n=3; wild-type, n=3). After completion of the PET scans, the mice were sacrificed at 60 min post injection. Radioactivity of the excised hearts was measured by well counter.

(x) Sertoli, Leydig, Epididymis, and Ovarian Cells

Figure 11:
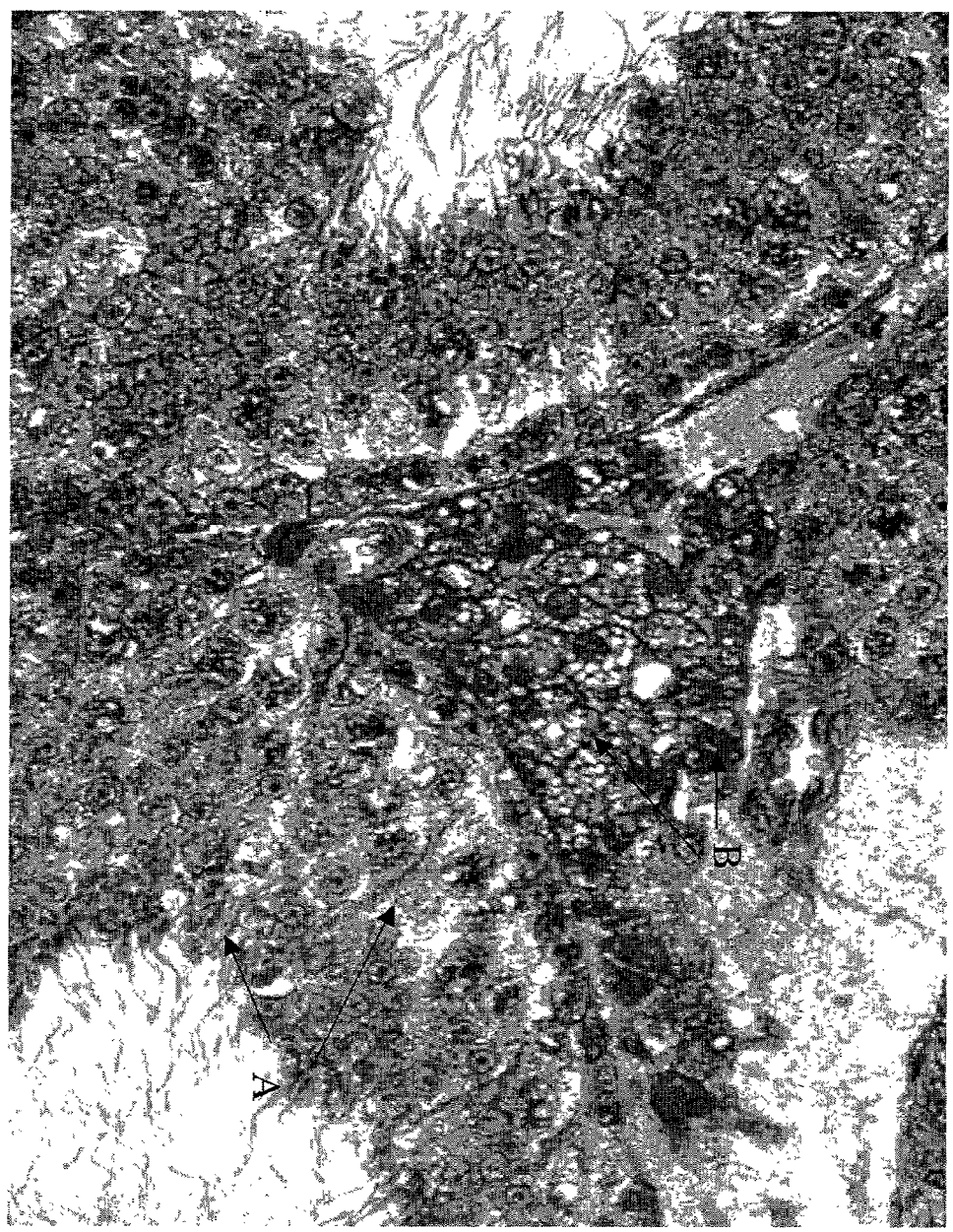
FIG. 11 demonstrates the immunolocalization of GLUTx. A: Sertoli cells, which nurture and support spermatogenesis, showed cytoplasmic staining for GLUTx. B: Leydig cells, which produce testosterone, exhibited intense staining for GLUTx in the vacuolar membrane, in the cytoplasm, and in what appears (with light microscopy) to be the cell membrane.

Immunocytochemistry was performed, as described above, on mouse testis (FIG. 11), rat epididymis (FIG. 12), and mouse ovary (data not shown), using the AEC chromogen on paraffin-embedded tissue.

2. Results and Discussion

The inventors hypothesize that the novel transporter molecule, GLUTx (also known as GLUTx1 and GLUT8), plays a central role in maintaining a balance between the utilization of substrate for energy, and the anabolic processes in the cell. Furthermore, it is believed that GLUTx expression itself may be regulated by the redox and nutritional status of the cell.

In the altered metabolic states of cancer and ischemia, the flow of blood is restricted, thereby affecting the availability of oxygen and nutrients. In such instances, the expression of GLUTx may be an adaptive feature which allows the cells efficiently to utilize available substrates. Similarly, in reproduction, sperm are exposed to different levels of oxygen and nutrients, in developing from spermatocytes to capacitated sperm able to move and fertilize the eggs (8–11). In such circumstances, the expression of GLUTx also may be an adaptive feature, allowing the sperm to use various energy sources (e.g., lactate, pyruvate, fructose, glucose) to survive and move in ever-changing nutrient and oxygen conditions.

(i) Cancer

Figure 2:
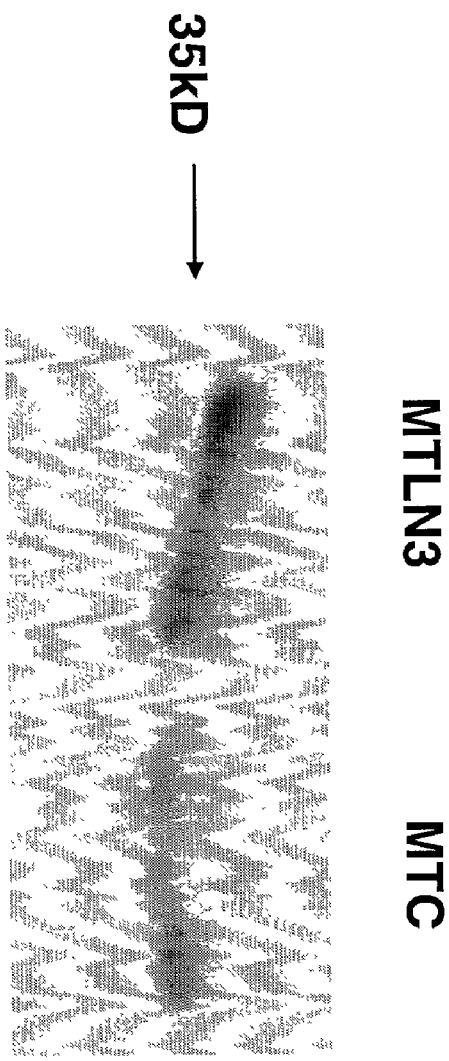
FIG. 2 shows an immunoblot analysis for GLUTx content in cultured tumor cells. $3 \times 10^6$ MTLn3 cells and $3 \times 10^6$ MTC cells were homogenized, and 60 µg of protein were analyzed. MTLn3 cells are rat mammary adenocarcinoma cells that are metastatic; MTC cells are non-metastatic rat mammary adenocarcinoma cells when transplanted subcutaneously into rats. This blot demonstrates that GLUTx is 3-fold more abundant in MTLn3 cells than in MTC cells. GLUTx is shown at approximately 35 kD.

The results of the inventor' experiments show that GLUTx is highly expressed in rodent and human cancer. Cancer cells exhibit increased glucose metabolism favoring glycolysis—a process that is adaptive for surviving in an environment with low blood flow or hypoxia (12–13). The inventors determined the GLUTx content in samples from murine tumors that were generated by overexpression of the oncogenes neu (a receptor), myc (a transcription factor), and ras (a GTPase) (FIG. 1). These oncogenes affect glucose metabolism in different ways (14). Myc regulates the expression of glucose transporters and glycolytic enzymes (15). FIG. 1 shows that, of the three tumor types, the myc tumors contain the most GLUTx. The expression of GLUTx is significantly higher in the more aggressive, metastasizing MTLn3 cells than in the non-aggressive, more differentiated MTC cells, as determined by immunoblot analysis of protein from an equal number of MTC and MTLn3 cells (FIG. 2).

With light microscopy, it appears that the distribution of GLUTx changes from a perinuclear distribution, to a distribution more associated with the cell membrane, to a distribution throughout the tumor cell (including the cell membrane). For example, based upon an immunohistochemical analysis of MTLn3 cells, it appears that GLUTX is distributed in the perinuclear Golgi region of MTLn3 cells in the basal state, and is also associated with the cell membrane (as viewed by light microscopy) of MTLn3 cells in the insulin-stimulated state (data not shown). Similarly, based upon an immunohistochemical analysis of MTC cells that stained for GLUTx, it appears that GLUTx is located mainly in the perinuclear Golgi region of MTC cells in the basal, normoxic state (data not shown). However, after MTC cells have been in the insulin-stimulated state for 1 h, light microscopy appears to show GLUTx localized also on the cell membrane (data not shown). Finally, GLUTx is highly expressed, and appears to be localized at the cell membrane, in MTC cells that have been hypoxic for 1 h (data not shown). Thus, under insulin stimulation, GLUTx appears to concentrate at the cell membranes of MTC and MTLn3 cells, and GLUTx expression is very high in MTC and MTLn3 cells which are exposed to hypoxia (data not shown).

Figure 3:
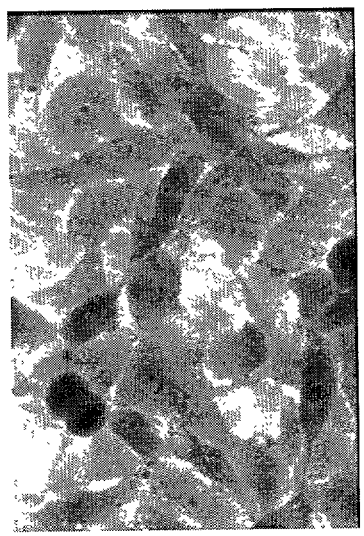
FIG. 3 sets forth immunostaining with GLUTx of MTC and MTLn3 tumor cells cultured with BRL49653, a thiazolidinedione. Panel A: MTC cells; Panel B: MTC cells incubated in 40 µM BRL49653; Panel C: MTLn3 cells; Panel D: MTLn3 cells incubated in 40 µM BRL49653.
Figure 3:
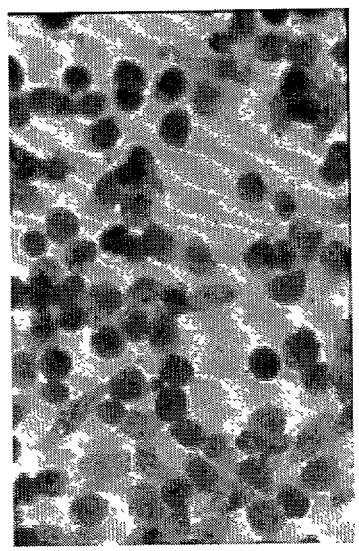
Figure 3:
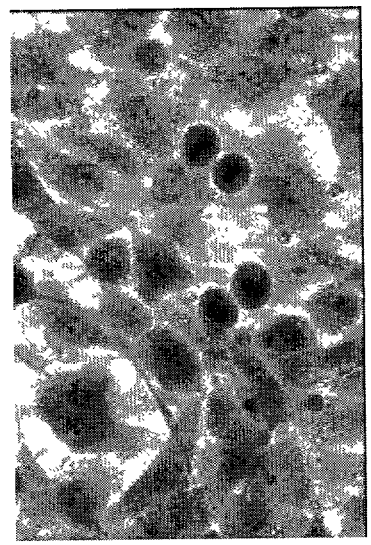
Figure 3:
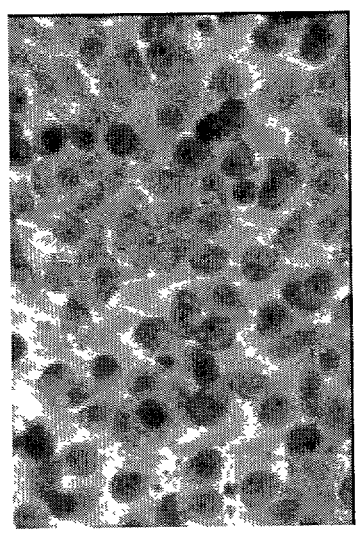
Figure 4:
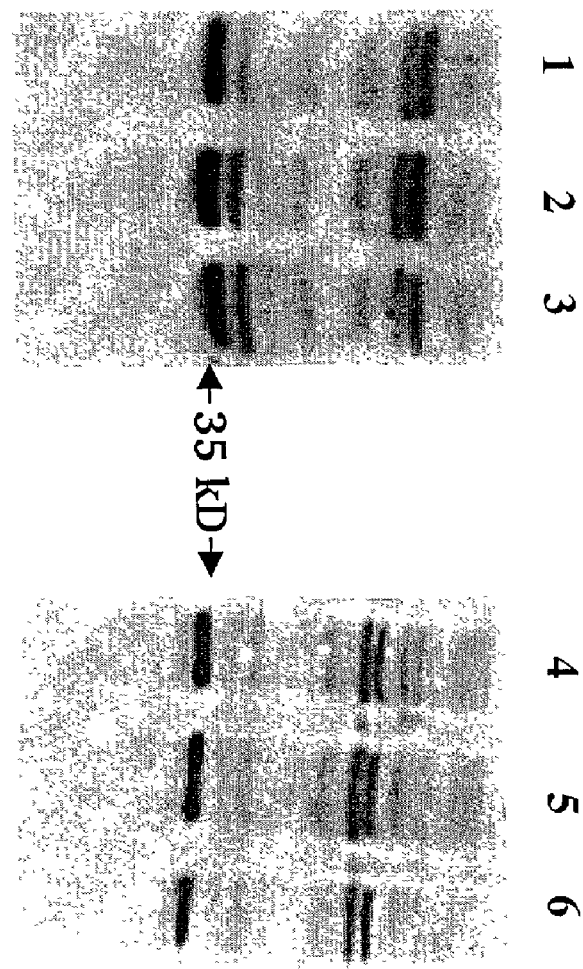
FIG. 4 shows an immunoblot analysis of GLUTx protein expression in MTC and MTLn3 cells. GLUTx is shown at approximately 35 kD. The band of higher molecular weight above 35 kD is nonspecific, and has not been shown to compete with immunizing peptide. Lane 1: MTC cells cultured in media with 2-µl vehicle (DMSO); Lane 2: MTC cells cultured in 10 µM BRL49653; Lane 3: MTC cells cultured in 40 µM BRL49653; Lane 4: MTLn3 cells cultured in media with 2-µl vehicle (DMSO); Lane 5: MTLn3 cells cultured in 10 µM BRL49653; Lane 6: MTLn3 cells cultured in 40 µM BRL49653

When MTC and MTLn3 cells were exposed to 40 $\mu$M BRL49653, a thiazolidinedione (TZD), the expression of GLUTx was altered in contrasting ways. BRL49653 is rosiglitizone—a ligand for the transcription factor PPAR$\gamma$ (16). PPAR$\gamma$ controls the expression of many genes involved in glucose metabolism, including those that code for glucose transporters and enzymes of glycolysis. When human breast cancer cells are exposed to TZDs, they stop dividing and develop a more differentiated phenotype (17). MTC cells exposed to 40 $\mu$M BRL49653 (dissolved in DMS0) for 4 days expressed more GLUTx than did cells cultured in media (plus 2 $\mu$l of DMSO, vehicle) (FIGS. 3 and 4). In contrast, the metastasizing cell line, MTLn3, shows a decrease in GLUTX expression under the same conditions.

Figure 5:
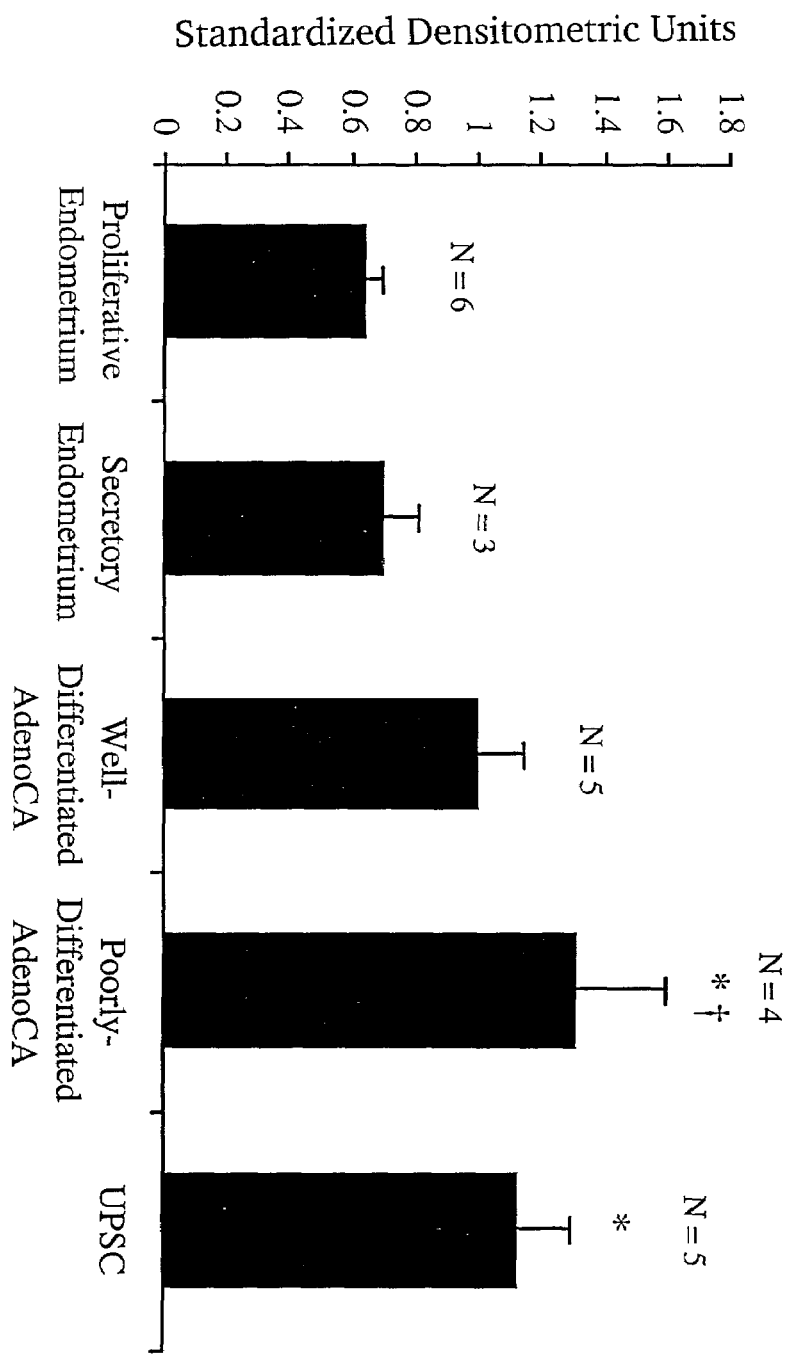
FIG. 5 sets forth a quantitative analysis of the 35-kD immunoreactive species of GLUTx in various types of human endometrial tissues. GLUTx protein expression is significantly higher in poorly-differentiated endometrial adenocarcinoma, as compared with both proliferative endometrium (†) and secretory endometrium (*). Uterine papillary serous carcinoma (UPSC) tumors had significantly higher GLUTx expression, as compared with proliferative endometrium (*). UPSC are highly aggressive tumors. *=p<0.05; †=p<0.01

The inventors also have assessed GLUTx levels in human benign proliferative endometrium and endometrial cancer (FIG. 5). Significantly more GLUTx was found in the adenocarcinomas, particularly the aggressive metastatic form, than in the proliferative disease. In view of these results, the inventors suggest that expression of GLUTx is upregulated in more aggressive metastasizing cancers, and that a high expression of GLUTx may be necessary to maintain this phenotype.

Semi-quantitative RT-PCR also was performed on small samples of human skeletal muscle and normal, dysplastic, and malignant endometrium. Primers specific for a 3' region of GLUTx cDNA were used, and the expected 351 base-pair fragment was successfully amplified in these human samples. This study revealed that GLUTx may be detected by RT-PCR in small samples of human tissue.

(ii) Ischemia/Reperfusion Injury

Figure 6:
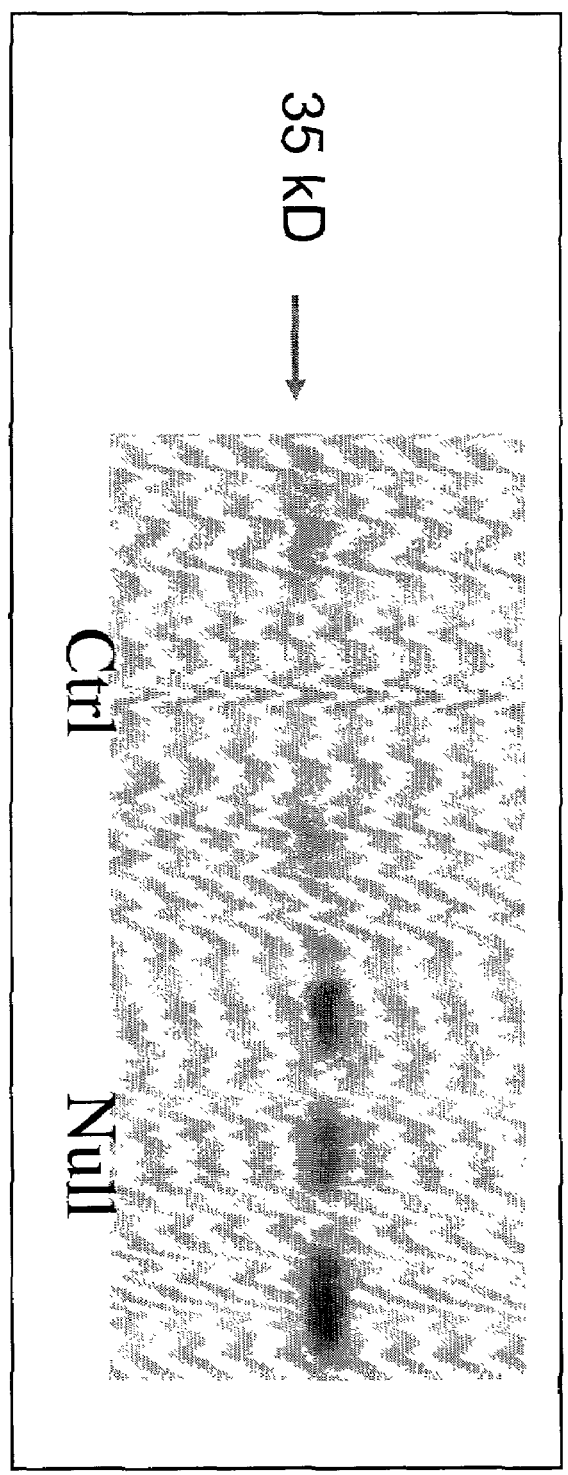
FIG. 6 shows an immunoblot analysis of GLUTx in GLUT4-null hearts and control hearts. GLUTx is significantly more abundant in GLUT4-null hearts than in control hearts (p<0.05). This overexpression of GLUTx could partially explain why the null heart takes up as much glucose as, or more glucose than, control hearts. GLUTx is shown at approximately 35 kD.

The inventors have determined by immunoblot analysis that GLUTx is more abundant in the GLUT4-null heart than in control hearts (FIG. 6). Hearts from wild-type and GLUT4-null mice were perfused in a Langendorff apparatus under isovolumic conditions controlled by a left ventricular balloon, and exposed to 20 min of ischemia and 40 min of reperfusion. Results of in vitro Langendorff perfusions show that GLUT4-null hearts take up normal amounts of glucose under basal conditions, but increased amounts of glucose, as compared with controls, under insulin-stimulated conditions (11). Yet, the GLUT4-null heart lacks the major glucose transporter of the heart, GLUT4.

Positron Emission Tomography (PET) images of 18-fluoro-2-deoxyglucose (FDG) uptake into control and null hearts show that, in the fasted animals, PET cannot detect FDG in either the control or the GLUT4-null heart. However, 1 h after a 1 g/kg dose of glucose, and an 8-unit/kg injection of insulin, more glucose is seen in the null heart than in the control (FIG. 7). A PET scan of fed animals after a short (90-min) stimulation with insulin shows significantly more FDG in the GLUT4-null heart (FIG. 8).

When the GLUT4-null hearts are made ischemic in vitro, they recover and maintain a level of function higher than that of control hearts (FIG. 9). In addition, the region of damage within the risk area following infarct is significantly smaller in GLUT4-null animals than in controls (FIG. 10). The inventors hypothesize that the upregulation of GLUTx is part of a gene-expression pattern in the GLUT4-null hearts that preconditions the cardiomyocytes to resist apoptosis/cell death, necrosis, and the damage caused by ischemia and reperfusion.

(iii) Reproductive Biology

Figure 12:
FIG. 12 sets forth an immunohistochemical analysis of GLUTx in a cross-section of distal cauda of rat epididymis. GLUTx (arrows) is highly expressed in the epithelial cells lining the epididymis.
Figure 13:
FIG. 13 is an immunoblot of GLUTx in rat sperm membranes. 100 µg of rat sperm membranes were loaded onto an SDS-PAGE gel, and immunoblotted for GLUTx. GLUTx can be seen in a band at approximately 35 kD.

Immunoblot and immunohistochemistry analyses showed that GLUTx is highly expressed in rodent Leydig cells and Sertoli cells of the testis (FIG. 11) and the epithelial cells of the epididymis (FIG. 12). An immunoblot of sperm membranes shows that GLUTx is also expressed in the sperm (FIG. 13). As FIG. 11 demonstrates, GLUTx is expressed in the Leydig cells and Sertoli cells of the testis. Leydig cells produce testosterone, which stimulates and supports spermatogenesis. Sertoli cells provide nutritional support and secrete androgen-binding protein and inhibin when stimulated by follicle stimulating hormone and testosterone. The epididymis also expresses GLUTx in its epithelial cells. This epithelial lining probably helps to create the ideal fluid environment for the continuing maturation of sperm. The sperm acquire motility and the ability to fertilize the eggs in the epididymis. Finally, the sperm themselves also express GLUTx (FIG. 13). This expression may be involved in regulating the substrates available for glycolysis and oxidation, in order to provide energy for sperm motility.

GLUTx can transport many different substrates (6). The inventors hypothesize that GLUTx participates in exporting from the Sertoli cells nutrients for the developing sperm (e.g., lactate and pyruvate) (8). These same substrates can be taken up by the sperm through GLUTx. Glycolysis in sperm is necessary for sperm to be capable of fertilizing eggs (18). Thus, if there is a disruption or decrease in the expression of GLUTx in the testis, epididymis, or sperm, the products of glycolysis will be decreased, and the process of sperm maturation and motility will be affected.

In the testis, GLUTX mRNA expression has been shown to be turned on at puberty, and to be turned off in testicular cancer and by estrogen treatment in humans (5). These results suggest that GLUTx is gonadotropin-responsive, and that it may play an important role in testis function and in spermatogenesis. On this basis, the inventors further propose that GLUTx may be regulated in human ovary in a similar manner.

Insulin and gonadotropins work as cofactors in vivo, inducing ovarian steroidogenesis to support oocyte maturation (38, 39). Insulin enhances the effect of follicle stimulating hormone (FSH) on aromatization in granulosa cells in vitro, and potentiates the luteinizing hormone (LH) stimulated production of estrogen and progesterone (40). In women with polycystic ovary syndrome (PCOS)—a disease associated with anovulatory infertility—insulin has been found to increase LH-induced androgen production in the theca (41). Similarly, in vitro, insulin and insulin-like growth factor stimulated testosterone biosynthesis by human thecal cells (42).

Using immunohistochemistry on mouse ovary, the inventors have localized GLUTx to the steroidogenic granulosa and the thecal cells, as well as the interstitial cells that represent thecal precursors (data not shown). It appears that GLUTx expression in granulosa cells is much higher in primary and secondary follicles than in granulosa lutein. The granulosa cells and thecal cells that are dsyfunctional in PCOS are the cells that exhibit the highest expression of GLUTx in the mouse ovary.

References Cited

1. Katz et al., Cardiac and adipose tissue abnormalities but not diabetes in mice deficient in GLUT4. *Nature,* 377: 151–55, 1995.
2. Kahn, B. B., Glucose transport: pivotal step in insulin action. *Diabetes,* 45:1644–54, 1996.
3. Stenbit et al., Diverse effects of Glut 4 ablation on glucose uptake and glycogen synthesis in red and white skeletal muscle. *J. Clin. Invest.,* 98:629–34, 1996.
4. Carayannopoulos et al., GLUT8 is a glucose transporter responsible for insulin-stimulated glucose uptake in the blastocyst. *Proc. Natl. Acad. Sci. U.S.A.,* 97:7313–18, 2000.
5. Doege et al., GLUT8, a novel member of the sugar transport facilitator family with glucose transport activity. *J. Biol. Chem.,* 275:16275–80, 2000.
6. Ibberson et al., GLUTx1, a novel mammalian glucose transporter expressed in the central nervous system and insulin-sensitive tissues. *J. Biol. Chem.,* 275:4607–12, 2000.
7. Reagan et al., Localization and regulation of GLUTx1 glucose transporter in the hippocampus of streptozotocin diabetic rats. *Proc. Natl. Acad. Sci.* U.S.A., 98:2820–26, 2001.
8. Guma et al., Effect of FSH and insulin on lipogenesis in cultures of Sertoli cells from immature rats.*Braz. J. Med. Biol. Res.,* 30:591–97, 1997.
9. Abou-Haila and Tulsiani, Mammalian sperm acrosome: formation, contents, and function. *Arch. Biochem. Biophys.,* 379:173–82, 2000.
10. Sutton, K. A., Molecular mechanisms involved in the differentiation of spermatogenic stem cells. *Rev. Reprod.,* 5:93–98, 2000.
11. Stenbit et al., Preservation of glucose metabolism in hypertrophic GLUT4 Null hearts. *Am. J. Physiol.,* 2000.
12. Warburg, O., On the origin of cancer cells. *Science,* 123:309–14, 1956.
13. Baggetto, L. G., Deviant energetic metabolism of glycolytic cancer cells. *Biochimie,* 74:959–74, 1992.
14. Kunz-Schughart et al., Proliferative activity and tumorigenic conversion: impact on cellular metabolism in 3-D culture. *Am. J. Physiol. Cell Physiol.,* 278:C765–80, 2000.

15. Spitz et al., Glucose deprivation-induced oxidative stress in human tumor cells. A fundamental defect in metabolism? *Ann. N.Y. Acad. Sci.,* 899:349–62, 2000.
16. Patel et al., Rosiglitizone monotherapy improves glycaemic control in patients with type 2 diabetes: a twelve-week, randomized, placebo-controlled study. *Diabetes Obes. Metab.,* 1:165–77, 1999.
17. Mueller et al., Terminal differentiation of human breast cancer through PPAR gamma. *Mol. Cell,* 1:465–70, 1998.
18. Bone et al., Effect of ornidazole on fertility of male rats: inhibition of a glycolysis-related motility pattern and zona binding required for fertilization in vitro. *J. Reprod. Fertil.,* 118:127–35, 2000.
19. Devaskar and Mueckler, The mammalian glucose transporters. *Pediatr. Res.,* 31:1–13, 1992.
20. Klip et al., Insulin-induced translocation of glucose transporters in rat hindlimb muscles. *FEBS letters,* 224:224–30, 1987.
21. Hirshman et al., Identification of an intracellular pool of glucose transporters from basal and insulin-stimulated rat skeletal muscle. *J. Biol. Chem.,* 265:987–91, 1990.
22. Cushman and Salans, Determinations of adipose cell size and number in suspensions of isolated rat and human adipose cells. *J. Lipid. Res.,* 19:269–73, 1978.
23. Douen et al., Exercise induces recruitment of the "insulin-responsive glucose transporter". Evidence for distinct intracellular insulin- and exercise-recruitable transporter pools in skeletal muscle. *J. Biol. Chem.,* 265:13427–30, 1990.
24. Cartee et al., Stimulation of glucose transport in skeletal muscle by hypoxia. *J. Appl. Physiol.,* 70:1593–1600, 1991.
25. Zierath et al., Restoration of hypoxia-stimulated glucose uptake in GLUT4-deficient muscles by muscle-specific GLUT4 transgenic complementation. *J. Biol. Chem.,* 273:20910–15, 1998.
26. Kamohara et al., Acute stimulation of glucose metabolism in mice by leptin treatment. *Nature,* 389:374–77, 1997.
27. Massillon et al., Quantitation of hepatic glucose fluxes and pathways of hepatic glycogen synthesis in conscious mice. *Am. J. Physiol.,* 269:E1037–43, 1995.
28. Tsao et al., Enhanced insulin action due to targeted GLUT4 overexpression exclusively in muscle. *Diabetes,* 45:28–36, 1996.
29. Chan and Exton, A rapid method for the determination of glycogen content and radioactivity in small quantities of tissue or isolated hepatocytes. *Anal. Biochem.,* 71:96–105, 1976.
30. Abe et al., Hypertension, hypertriglyceridemia, and impaired endothelium-dependent vascular relaxation in mice lacking insulin receptor substrate-1. *J. Clin. Invest.,* 101:1784–88, 1998.
31. Cuendet et al., Decreased basal, noninsulin-stimulated glucose uptake and metabolism by skeletal soleus muscle isolated from obese-hyperglycemic (ob/ob) mice. *J. Clin. Invest.,* 58:1078–88, 1976.
32. Karl et al., Effect of insulin on glucose utilization in epitrochlearis muscle of rats with streptozotocin-induced NIDDM. *Diabetes,* 39:1106–15, 1990.
33. Scherer et al., Induction of caveolin during adipogenesis and association of GLUT4 with caveolin-rich vesicles. *J. Cell Biol.,* 127:1233–43, 1994.
34. Li et al., Expression and signal transduction of the glucagon receptor in betaTC3 cells. *Biochim. Biophys. Acta,* 1356:229–36, 1997.
35. Ryder et al., In vitro analysis of the glucose-transport system in GLUT4-null skeletal muscle. *Biochem. J.,* 342:321–28, 1999.
36. Neri et al., Development and biologic properties of malignant cell sublines and clones of a spontaneously metastasizing rat mammary adenocarcinoma. *J. Natl. Cancer Inst.,* 68:507–17, 1982.
37. Miao et al., Intracoronary, adenovirus-mediated Akt gene transfer in heart limits infarct size following ischemia-reperfusion injury in vivo. *J. Mol. Cell. Cardiol.,* 32:2397–402, 2000.
38. Adashi et al., Insulin-like growth factors as intraovarian regulators of granulosa cell growth and function. *Endocr. Rev.,* 6:400–20, 1985.
39. Erikson et al., The effects of insulin and insulin-like growth factors –1 and -II on estradiol production by granulosa cells of polycystic ovaries. *J. Clin. Endocrinol. Metabol.,* 70:894–902, 1990.
40. Dunaif et al., Excessive insulin receptor serine phophorylation in cultured fibroblasts and skeletal muscle. A potential mechanism for insulin resistance in the polycystic ovary syndrome. *J. Clin. Invest.,* 96(2):801–10, 1995.
41. Kim et al., Insulin sensitizers and polycystic ovary syndrome: can a diabetes medication treat infertility? *Fertil. Steril.,* 73(6):1097–98, 2000.
42. Nestler et al., Insulin stimulates testosterone biosynthesis by human thecal cells from women with polycystic ovary syndrome by activating its own receptor and using inositolglycan mediators as the signal transduction system. *J. Clin. Endocrinol. Metab.,* 83(6):2001–05, 1998.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for determining whether a subject has a defect in cell proliferation comprising assaying a diagnostic sample of the subject for GLUTx expression wherein detection of GLUTx expression elevated above normal is diagnostic of a defect in cell proliferation, wherein the defect in cell proliferation is a mammary adenocarcinoma or an endometrial adenocarcinoma, wherein GLUTx protein consists of the amino acid sequence set forth in SEQ ID NO:1, and wherein the diagnostic sample is assayed using an antibody that specifically binds to GLUTx protein.

2. The method of claim 1, wherein the antibody is labeled with a detectable marker.

3. A method for determining whether a subject has a defect in cell proliferation comprising assaying a diagnostic sample of the subject for GLUTx expression wherein detection of GLUTx expression elevated above normal is diagnostic of a defect in cell proliferation, wherein the defect in cell proliferation is a mammary adenocarcinoma or an endometrial adenocarcinoma, wherein GLUTx protein consists of the amino acid sequence set forth in SEQ ID NO:1, and wherein the diagnostic sample is assayed using at least one nucleic acid probe that specifically hybridizes to nucleic acid encoding GLUTx.

4. The method of claim 3, wherein the nucleic acid probe is DNA or RNA.

5. The method of claim 4, wherein the nucleic acid probe is labeled with a detectable marker.

6. A method for assessing the efficacy of therapy to treat a defect in cell proliferation in a subject who has undergone or is undergoing treatment for a defect in cell proliferation, comprising assaying a diagnostic sample of the subject for GLUTx expression, wherein detection of GLUTx expression elevated above normal in the diagnostic sample is indicative of a need to continue therapy to treat the defect in cell proliferation, and normal GLUTx expression in the diagnostic sample is indicative of successful therapy, wherein the defect in cell proliferation is a mammary adenocarcinoma or an endometrial adenocarcinoma, and wherein GLUTx protein has the amino acid sequence set forth in SEQ ID NO:1.

7. The method of claim 6, wherein the diagnostic sample is assayed using an antibody reactive with GLUTx protein.

8. The method of claim 7, wherein the antibody is labeled with a detectable marker.

9. The method of claim 6, wherein the diagnostic sample is assayed using at least one nucleic acid probe which hybridizes to nucleic acid encoding GLUTx.

10. The method of claim 9, wherein the nucleic acid probe is DNA or RNA.

11. The method of claim 10, wherein the nucleic acid probe is labeled with a detectable marker.

* * * * *

UNITED STATES PATENT AND TRADEMARK OFFICE
CERTIFICATE OF CORRECTION

PATENT NO. : 7,001,735 B2  
APPLICATION NO. : 09/886954  
DATED : February 21, 2006  
INVENTOR(S) : Maureen J. Charron and Ellen B. Katz Page 1 of 1

It is certified that error appears in the above-identified patent and that said Letters Patent is hereby corrected as shown below:

In the specification

In Column 1, line 10 after the title, please add:

-- STATEMENT OF GOVERNMENT SUPPORT

This invention was made with government support under grant numbers DK047425 and HL058119 awarded by the National Institutes of Health. The government has certain rights in the invention. --

Signed and Sealed this
Seventeenth Day of November, 2015

Michelle K. Lee
*Director of the United States Patent and Trademark Office*